US006951856B2

(12) United States Patent
Boss et al.

(10) Patent No.: US 6,951,856 B2
(45) Date of Patent: Oct. 4, 2005

(54) ARYLETHENE-SULFONAMIDES

(75) Inventors: Christoph Boss, Allschwil (CH); Martin Bolli, Allschwil (CH); Martine Clozel, Saint-Louis (FR); Walter Fischli, Allschwil (CH); Thomas Weller, Binningen (CH)

(73) Assignee: Actelion Pharmaceuticals Ltd. (CH)

( * ) Notice: Subject to any disclaimer, the term of this patent is extended or adjusted under 35 U.S.C. 154(b) by 243 days.

(21) Appl. No.: 10/332,247

(22) PCT Filed: Jul. 10, 2001

(86) PCT No.: PCT/EP01/07922

§ 371 (c)(1),
(2), (4) Date: Jan. 3, 2003

(87) PCT Pub. No.: WO02/08200

PCT Pub. Date: Jan. 31, 2002

(65) Prior Publication Data

US 2003/0220359 A1 Nov. 27, 2003

(30) Foreign Application Priority Data

Jul. 21, 2000 (WO) .............................. PCT/EP00/07006

(51) Int. Cl.$^7$ ........................................... A61K 31/535
(52) U.S. Cl. ............................. 514/235.8; 514/255.05; 514/256; 514/269; 514/272; 544/122; 544/295; 544/296; 544/310; 544/311; 544/317
(58) Field of Search ................................ 544/122, 295, 544/296, 310, 311, 317, 319, 321, 327; 514/235.8, 256, 255.05, 269, 272

(56) References Cited

U.S. PATENT DOCUMENTS

| | | | | |
|---|---|---|---|---|
| 5,292,740 A | | 3/1994 | Burri et al. .................. | 514/256 |
| 5,420,129 A | | 5/1995 | Breu et al. .................. | 514/252 |

FOREIGN PATENT DOCUMENTS

| | | |
|---|---|---|
| EP | 0 526 708 | 2/1993 |
| EP | 0 633 259 | 1/1995 |
| EP | 0 658 548 | 6/1995 |
| EP | 0 743 307 | 11/1996 |
| EP | 0 882 719 | 12/1998 |
| EP | 0 959 072 | 11/1999 |
| WO | WO 00/42035 | 7/2000 |
| WO | WO 00/52007 | 9/2000 |

OTHER PUBLICATIONS

Simone, Oncology: Introduction, Cecil Textbook of Medicine, 20$^{th}$ Edition, vol. 1, pp. 1004–1010, 1996.*

Harada et al., Abstract (Ethenesulfonamide Derivatives, a Novel Class of Orally Active Endothelin–A Receptor Antagonists, Chem. Pharm. Bull., 49(5):606–612), May 2001.*

Harada et al., CAPLUS Abstract 135:122462, 2001.*

Schiffrin, Role of Endothelin–1 in Hypertension, Hypertension, Part II, pp. 876–881, Oct. 1999.*

Arai et al. Cloning and expression of a cDNA encoding an endothelin receptor. Nature. 1990 Dec. 20–27; 348(6303):730–2.

Arogba, S. S. Synthesis of primin and miconinin an dtheir 3–methoxy isomers. Organic Preparations and Procedures Int., 1991, 23(5):639–643.

Bhaskar Reddy et al. Phosphorous, Sulfur and Silicon., 1993, 84:63–71.

Bhaskar Reddy et al., Indian J. Chem., 1995, 34B:816–822.

Breu et al. In vitro characterization of Ro 46–2005, a novel synthetic non–peptide endothelin antagonist of ETA and ETB receptors. FEBS Lett. Nov. 15, 1993;334(2):210–4.

Culbertson et al. Some aromatic vinyl sulphonyl chlorides. J. Chem. Soc. (C), 1968, 992–993.

Douglas et al. Endothelin–1 does not mediate hypoxic vasoconstriction in canine isolated blood vessels: effect of BQ–123. Br J Pharmacol. Feb. 1993;108(2):418–21.

Fox et al. Highly active and selective catalysts for the formation of α–Aryl ketones. J. Am. Chem. Soc., 2000, 122:1360–1370.

Gohring et al. Development of a process to prepare 2–cyanopyrimidine on commercial scale. Chimia, 1996, 50:538–543.

Kameyama et al. Synthesis of substituted 1,3–Dienes by the Reaction of Alkenesulfonyl chlorides with olefins catalyzed by a ruthenium (II) complex. Bull. Chem. Soc. Jpn., 1988, 61:1231–1235.

Kohara et al. Synthesis and angiotensin II receptor antagonistic activities of benzimidazole derivatives bearing acidic heterocycles as novel tetrazole bioisosteres. J Med Chem. Dec. 20, 1996;39(26)5228–35.

Lonchambon et al. Bull. Soc. Chim. Fr., 1981, II–71 (in French with English Summary).

March, J. Advanced Organic Chemistry. 4$^{th}$ Ed., 1994, p. 499.

Matlack A.S. Preparation of ethenesulfonamide. J. Org. Chem., 1958, 23:729–31.

(Continued)

*Primary Examiner*—Deepak Rao
(74) *Attorney, Agent, or Firm*—Gibbons, Del Deo, Dolan, Griffinger & Vecchione

(57) ABSTRACT

The invention relates to novel aryl-ethene-sulfonamides and their use as active ingredients in the preparation of pharmaceutical compositions. The invention also concerns related aspects including processes for the preparation of the compounds, pharmaceutical compositions containing one or more of those compounds and especially their use as endothelin receptor antagonists.

38 Claims, No Drawings

OTHER PUBLICATIONS

McMillen et al. Endothelins: polyfunctional cytokines. J Am Coll Surg. May 1995;180(5):621–37. Review.

Neidhart et al. Discovery of RO 48–5695: A potent mixed endothelin receptor antagonist optimized from Bosentan. Bioorg. Med. Chem. Lett. 1997, 7:2223–2228.

Neidhart et al. The discovery of nonpeptide endothelin receptor antagonists. Progression towards Bosentan. Chimia 1996, 50:519–524.

Nugent et al. Pyrimidine thioethers: a novel class of HIV–1 reverse transcriptase inhibitors with activity against BHAP–resistant HIV. J Med Chem. Sep. 24, 1998;41(20):3793–803.

Ogawa et al. Molecular cloning of a non–isopeptide–selective human endothelin receptor. Biochem Biophys Res Commun. Jul. 15, 1991;178(1):248–55.

Ramana Reddy et al. A new route for the synthesis of styrylbenzylsulfones, precursors of 1–benzylsulfonyl–2–arylcyclopropanes. Phosphorous Sulfur and Silicon. 1990, 53:285–290.

Rubanyi et al. Endothelins: molecular biology, biochemistry, pharmacology, physiology, and pathophysiology. Pharmacol Rev. Sep. 1994;46(3):325–415. Review.

Sumner et al. Endothelin ETA and ETB receptors mediate vascular smooth muscle contraction. Br J Pharmacol. Nov. 1992;107(3):858–60.

Yanagisawa et al. A novel potent vasoconstrictor peptide produced by vascular endothelial cells. Nature. Mar. 31, 1998;332(6163):411–5.

Bull. Chem Soc. Jpn., 1991, 64:1431.

* cited by examiner

ARYLETHENE-SULFONAMIDES

The present invention relates to novel arylethene-sulfonamides of the general formula I and their use as active ingredients in the preparation of pharmaceutical compositions. The invention also concerns related aspects including processes for the preparation of the compounds, pharmaceutical compositions containing one or more compounds of the general formula I and especially their use as endothelin antagonists.

Endothelins (ET-1, ET-2, and ET-3) are 21-amino acid peptides produced and active in almost all tissues (Yanagisawa M et al.: Nature (1988) 332:411). Endothelins are potent vasoconstrictors and important mediators of cardiac, renal, endocrine and immune functions (McMillen M A et al.: J Am Coil Surg (1995) 180:621). They participate in bronchoconstriction and regulate neurotransmitter release, activation of inflammatory cells, fibrosis, cell proliferation and cell differentiation (Rubanyi G M et al.: Pharmacol Rev (1994) 46:328).

Two endothelin receptors have been cloned and characterized in mammals ($ET_A$, $ET_B$) (Arai H et al.: Nature (1990) 348:730; Sakurai T et al.: Nature (1990) 348:732). The $ET_A$ receptor is characterized by higher affinity for ET-1 and ET-2 than for ET-3. It is predominant in vascular smooth muscle cells and mediates vasoconstricting and proliferative responses (Ohlstein E H et al.: Drug Dev Res (1993) 29:108). In contrast, the $ET_B$ receptor has equivalent affinity for the 3 endothelin isopeptides and binds the linear form of endothelin, tetra-ala-endothelin, and sarafotoxin S6C (Ogawa Y et al.: BBRC (1991) 178:248). This receptor is located in the vascular endothelium and smooth muscles, and is also particularly abundant in lung and brain. The $ET_B$ receptor from endothelial cells mediates transient vasodilator responses to ET-1 and ET-3 through the release of nitric oxide and/or prostacyclin whereas the $ET_B$ receptor from smooth muscle cells exerts vasoconstricting actions (Sumner M J et al.: Brit J Pharmacol (1992) 107:858). $ET_A$ and $ET_B$ receptors are highly similar in structure and belong to the superfamily of G-protein coupled receptors.

A pathophysiological role has been suggested for ET-1 in view of its increased plasma and tissue levels in several disease states such as hypertension, sepsis, atherosclerosis, acute myocardial infarction, congestive heart failure, renal failure, migraine and asthma. As a consequence, endothelin receptor antagonists have been studied extensively as potential therapeutic agents. Endothelin receptor antagonists have demonstrated preclinical and/or clinical efficacy in various diseases such as cerebral vasospasm following subarachnoid hemorrhage, heart failure, pulmonary and systemic hypertension, neurogenic inflammation, renal failure and myocardial infarction.

Today, no endothelin receptor antagonist is marketed yet, several are in clinical trials. However, these molecules possess a number of weaknesses such as complex synthesis, low solubility, high molecular weight, poor pharmacokinetics, or safety problems (e.g. liver enzyme increases).

The inhibitory activity of the compounds of general formula I on endothelin receptors can be demonstrated using the test procedures described hereinafter:

For the evaluation of the potency and efficacy of the compounds of the general formula I the following tests were used:

1) Inhibition of Endothelin Binding to Membranes from CHO Cells Carrying Human ET Receptors For competition binding studies, membranes of CHO cells expressing human recombinant $ET_A$ or $ET_B$ receptors were used. Microsomal membranes from recombinant CHO cells were prepared and the binding assay made as previously described (Breu V., et al, FEBS Lett 1993; 334:210).

The assay was performed in 200 uL 50 mM Tris/HCl buffer, pH 7.4, including 25 mM $MnCl_2$, 1 mM EDTA and 0.5% (w/v) BSA in polypropylene microtiter plates. Membranes containing 0.5 ug protein were incubated for 2 h at 20° C. with 8 pM [$^{125}$I]ET-1 (4000 cpm) and increasing concentrations of unlabelled antagonists. Maximum and minimum binding were estimated in samples without and with 100 nM ET-1, respectively. After 2 h, the membranes were filtered on filterplates containing GF/C filters (Unifilterplates from Canberra Packard S.A. Zürich, Switzerland). To each well, 50 uL of scintillation cocktail was added (MicroScint 20, Canberra Packard S.A. Zürich, Switzerland) and the filter plates counted in a microplate counter (TopCount, Canberra Packard S.A. Zürich, Switzerland).

All the test compounds were dissolved, diluted and added in DMSO. The assay was run in the presence of 2.5% DMSO which was found not to interfere significantly with the binding. $IC_{50}$ was calculated as the concentration of antagonist inhibiting 50% of the specific binding of ET-1. For reference compounds, the following $IC_{50}$ values were found: $ET_A$ cells: 0.075 nM (n=8) for ET-1 and 118 nM (n=8) for ET-3; $ET_B$ cells: 0.067 nM (n=8) for ET-1 and 0.092 nM (n=3) for ET-3.

The $IC_{50}$ values obtained with compounds of general formula I are given in Table 1.

TABLE 1

| Compound of Example | $IC_{50}$[nM] $ET_A$ | $ET_B$ |
|---|---|---|
| Example 1 | 1.8 | 569 |
| Example 2 | 25.4 | 1835 |
| Example 3 | 46.3 | 722 |
| Example 6 | 82.4 | 1351 |
| Example 13 | 28.7 | 3989 |
| Example 4 | 273.4 | 8605 |
| Example 11 | 18.53 | 264.2 |
| Example 12 | 52.1 | 532 |
| Example 5 | 12.8 | 129.5 |
| Example 14 | 4.75 | 841 |
| Example 15 | 17.98 | 2129 |
| Example 16 | 62.2 | 1125 |
| Example 21 | 14.67 | 749 |
| Example 23 | 8.2 | 270 |
| Example 24 | 21.7 | 657 |
| Example 27 | 11.5 | 193 |
| Example 30 | 41.8 | 9075 |
| Example 36 | 20 | 3392 |
| Example 40 | 6.2 | 629 |
| Example 41 | 5.4 | 1781 |
| Example 43 | 4.6 | 408 |
| Example 45 | 19.3 | 332 |
| Example 46 | 41.7 | 541 |
| Example 47 | 7.04 | 752 |
| Example 48 | 10.6 | 832 |
| Example 49 | 27.2 | 4143 |
| Example 50 | 30.99 | 6894 |
| Example 51 | 4.56 | 173 |
| Example 52 | 7.5 | 1487 |
| Example 53 | 21 | 1362 |
| Example 54 | 14 | 183 |
| Example 58 | 24 | 277 |
| Example 60 | 30 | 558 |
| Example 62 | 58 | 4905 |
| Example 65 | 17 | 2517 |
| Example 67 | 7.8 | 752 |
| Example 69 | 6 | 1647 |
| Example 70 | 16 | 258 |

TABLE 1-continued

| Compound of Example | IC$_{50}$[nM] ET$_A$ | ET$_B$ |
|---|---|---|
| Example 71 | 17 | 507 |
| Example 72 | 9 | 2385 |
| Example 73 | 7.6 | 4757 |
| Example 74 | 7.8 | 3526 |
| Example 75 | 17.6 | >10000 |
| Example 80 | 19.7 | 2569 |
| Example 83 | 27.5 | 7589 |
| Example 85 | 3.8 | 238 |
| Example 86 | 4.6 | 193 |
| Example 87 | 3.9 | 439 |
| Example 88 | 6 | 496 |
| Example 89 | 4.6 | 1221 |
| Example 90 | 4.3 | 336 |
| Example 92 | 20 | 7470 |
| Example 95 | 33 | 8391 |
| Example 101 | 30.7 | 8682 |
| Example 104 | 54 | 8336 |
| Example 107 | 8.5 | 4645 |
| Example 109 | 39 | >10000 |
| Example 113 | 14.7 | >10000 |
| Example 114 | 18.4 | 3876 |
| Example 116 | 24.9 | >10000 |
| Example 117 | 7.9 | 4339 |
| Example 118 | 9.8 | 1005 |
| Example 119 | 55 | 735 |
| Example 120 | 38.7 | 1630 |
| Example 124 | 33.2 | 309 |
| Example 125 | 6.7 | 2700 |
| Example 126 | 9 | 3644 |
| Example 127 | 14.2 | 2755 |
| Example 132 | 5.7 | 1660 |
| Example 133 | 8.2 | 1770 |
| Example 134 | 6.3 | 4895 |
| Example 138 | 4.4 | 1335 |
| Example 139 | 9.8 | 1688 |
| Example 140 | 12.5 | 1090 |
| Example 144 | 10 | 3059 |
| Example 145 | 9.1 | 2385 |
| Example 146 | 7.8 | 3526 |
| Example 147 | 7.6 | 4757 |
| Example 152 | 43.3 | 4822 |
| Example 157 | 21.7 | 4505 |
| Example 158 | 12.1 | 1259 |
| Example 159 | 7.3 | 2277 |
| Example 160 | 12.9 | 757 |
| Example 164 | 10 | 1564 |
| Example 166 | 15 | 756 |
| Example 173 | 4.2 | 976 |
| Example 174 | 6.7 | 1010 |
| Example 175 | 4.7 | 499 |
| Example 176 | 4.1 | 1079 |
| Example 177 | 5.5 | 363 |
| Example 178 | 5 | 671 |
| Example 179 | 9 | 699 |
| Example 180 | 7.4 | 1027 |
| Example 181 | 7.1 | 1977 |
| Example 182 | 16.7 | 1405 |
| Example 193 | 2.6 | 537 |
| Example 194 | 7.8 | 627 |
| Example 195 | 6 | 293 |
| Example 196 | 4.7 | 427 |
| Example 197 | 5 | 220 |
| Example 198 | 7.9 | 595 |
| Example 202 | 2.4 | 349 |
| Example 203 | 3.4 | 249 |
| Example 204 | 3.3 | 138 |
| Example 211 | 38 | 2638 |
| Example 214 | 39 | 3942 |
| Example 222 | 41 | 506 |
| Example 225 | 5.2 | 830 |
| Example 226 | 15.4 | 1547 |
| Example 227 | 4.3 | 145 |
| Example 228 | 14.5 | 3911 |
| Example 230 | 12.3 | 937 |

TABLE 1-continued

| Compound of Example | IC$_{50}$[nM] ET$_A$ | ET$_B$ |
|---|---|---|
| Example 232 | 10 | 290 |
| Example 240 | 26 | 3126 |

2) Inhibition of Endothelin-Induced Contractions on Isolated Rat Aortic Rings (ET$_A$ Receptors) and Rat Tracheal Rings (ET$_B$ Receptors):

The functional inhibitory potency of the endothelin antagonists was assessed by their inhibition of the contraction induced by endothelin-1 on rat aortic rings (ET$_A$ receptors) and of the contraction induced by sarafotoxin S6c on rat tracheal rings (ET$_B$ receptors). Adult Wistar rats were anesthetized and exsanguinated. The thoracic aorta or trachea were excised, dissected and cut in 3–5 mm rings. The endothelium/epithelium was removed by gentle rubbing of the intimal surface. Each ring was suspended in a 10 ml isolated organ bath filled with Krebs-Henseleit solution (in mM; NaCl 115, KCl 4.7, MgSO$_4$ 1.2, KH$_2$PO$_4$ 1.5, NaHCO$_3$ 25, CaCl$_2$ 2.5, glucose 10) kept at 37° and gassed with 95% O$_2$ and 5% CO$_2$. The rings were connected to force transducers and isometric tension was recorded (EMKA Technologies SA, Paris, France). The rings were stretched to a resting tension of 3 g (aorta) or 2 g (trachea). Cumulative doses of ET-1 (aorta) or sarafotoxin S6c (trachea) were added after a 10 min incubation with the test compound or its vehicle. The functional inhibitory potency of the test compound was assessed by calculating the concentration ratio, i.e. the shift to the right of the EC$_{50}$ induced by different concentrations of test compound. EC$_{50}$ is the concentration of endothelin needed to get a half-maximal contraction, pA$_2$ is the negative logarithm of the antagonist concentration which induces a two-fold shift in the EC$_{50}$ value. The pA$_2$ values obtained with compounds of formula I are given in Table 2.

TABLE 2

| Compound of Example | pA$_2$ value ET$_A$ | ET$_B$ |
|---|---|---|
| Example 1 | 8.73 | 7.09 |
| Example 14 | 8.67 | |
| Example 15 | 7.57 | |
| Example 43 | 9.07 | |
| Example 67 | 9.5 | |
| Example 80 | 8.35 | 5.21 |
| Example 85 | 9.07 | |
| Example 92 | 7.91 | |
| Example 140 | 8.73 | |
| Example 152 | 7.69 | 6.04 |
| Example 173 | 8.83 | 7.1 |
| Example 174 | 7.88 | |
| Example 193 | 8.6 | 6.9 |
| Example 194 | 7.5 | 6.5 |
| Example 195 | 8.04 | |
| Example 196 | 7.68 | |
| Example 209 | 6.58 | |
| Example 211 | 7.61 | 6.65 |

Because of their ability to inhibit the endothelin binding, the described compounds can be used for treatment of diseases which are associated with an increase in vasoconstriction, proliferation or inflammation due to endothelin. Examples of such diseases are hypertension, coronary diseases, cardiac insufficiency, renal and myocardial ischemia, renal failure, cerebral ischemia, dementia, migraine, subarachnoidal hemorrhage, Raynaud's syndrome, portal hypertension and pulmonary hypertension. They can also be used for atherosclerosis, prevention of restenosis after balloon or stent angioplasty, inflammation, stomach and duodenal ulcer, cancer, prostatic hypertrophy, erectile dysfunction, hearing loss, amaurosis, chronic bronchitis, asthma, gram negative septicemia, shock, sickle cell anemia, glomerulonephritis, renal colic, glaucoma, therapy and prophylaxis of diabetic complications, complications of vascular or cardiac surgery or after organ transplantation, complications of cyclosporin treatment, pain as well as other diseases presently known to be related to endothelin.

The compounds can be administered orally, rectally, parenterally, e.g. by intravenous, intramuscular, subcutaneous, intrathecal or transdermal administration or sublingually or as ophthalmic preparation or administered as aerosol. Examples of applications are capsules, tablets, orally administered suspensions or solutions, suppositories, injections, eye-drops, ointments or aerosols/nebulizers.

Preferred applications are intravenous, intramuscular, or oral administrations as well as eye drops. The dosage used depends upon the type of the specific active ingredient, the age and the requirements of the patient and the kind of application. Generally, dosages of 0.1–50 mg/kg body weight per day are considered. The preparations with compounds can contain inert or as well pharmacodynamically active excipients. Tablets or granules, for example, could contain a number of binding agents, filling excipients, carrier substances or diluents.

The present invention relates to arylethene-sulfonamides of the general formula I, General Formula I

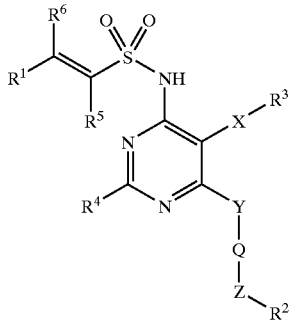

wherein $R^1$ and $R^2$ represent aryl; heteroaryl;

$R^3$ represents phenyl; mono-, di- or tri-substituted phenyl substituted with lower alkyl, lower alkenyl, lower alkynyl, phenyl, lower alkyloxy, amino, lower alkylamino, amino-lower alkyl, trifluoromethyl, trifluoromethoxy, halogen, lower alkylthio, hydroxy, hydroxy-lower alkyl, cyano, carboxyl, lower alkanoyl, formyl; benzofuranyl; aryl; heteroaryl;

$R^4$ represents hydrogen; halogen; trifluoromethyl; lower alkyl; lower alkyl-amino; lower alkyloxy; lower alkyl-sulfono; lower alkyl-sulfinyl; lower alkylthio; lower alkylthio-lower alkyl; hydroxy-lower alkyl; lower alkyl-oxy-lower alkyl; hydroxy-lower alkyl-oxy-lower alkyl; hydroxy-lower alkyl-amino; lower alkyl-amino-lower alkyl; amino; di-lower alkyl-amino; [N-(hydroxy-lower alkyl)-N-(lower alkyl)]-amino; aryl; aryl-amino; aryl-lower alkyl-amino; aryl-thio; aryl-lower alkyl-thio; aryloxy; aryl-lower alkyl-oxy; aryl-lower alkyl; aryl-sulfinyl; heteroaryl; heteroaryl-oxy; heteroaryl-lower alkyl-oxy; heteroaryl-amino; heteroaryl-lower alkyl-amino; heteroaryl-thio; heteroaryl-lower alkyl-thio; heteroaryl-lower alkyl; heteroaryl-sulfinyl; heterocyclyl; heterocyclyl-lower alkyl-oxy; heterocyclyl-oxy; heterocyclyl-amino; heterocyclyl-lower alkyl-amino; heterocyclyl-thio; heterocyclyl-lower alkyl-thio; heterocyclyl-lower alkyl; heterocyclyl-sulfinyl; cycloalkyl; cycloalkyl-oxy; cycloalkyl-lower alkyl-oxy; cycloalkyl-amino; cycloalkyl-lower alkyl-amino; cycloalkyl-thio; cycloalkyl-lower alkyl-thio; cycloalkyl-lower alkyl; cycloalkyl-sulfinyl;

$R^5$ and $R^6$ represent hydrogen or lower alkyl and may be the same or different;

X represents oxygen; sulfur; NH; $CH_2$ or a bond;

Y represents oxygen; sulfur or —NH—;

Z represents oxygen; sulfur, —NH— or a bond;

Q represents —$(CH_2)_n$—; —$(CH_2)_m$—C≡C—$(CH_2)_p$—, in case p represents the whole number O, Z represents a bond; —$CH_2$-cyclopropylen—$CH_2$—;

n represents the whole numbers 2, 3, 4, 5, 6;

m represents the whole numbers 1, 2 or 3;

p represents the whole numbers 0, 1, 2 or 3;

and pure diastereomers, mixtures of diastereomers, diastereomeric racemates, mixtures of diastereomeric racemates and the meso-forms and pharmaceutically acceptable salts thereof.

In the definitions of the general formula I—if not otherwise stated—the expression lower means straight and branched chain groups with one to seven carbon atoms, preferably 1 to 4 carbon atoms. Examples of lower alkyl and lower alkoxy groups are methyl, ethyl, n-propyl, isopropyl, n-butyl, isobutyl, sec.-butyl, tert.-butyl, pentyl, hexyl, heptyl, methoxy, ethoxy, propoxy, butoxy, iso-butoxy, sec.-butoxy and tert.-butoxy. Lower alkylendioxy-groups are preferably methylen-dioxy, ethylen-dioxy, propylen-dioxy and butylen-dioxy groups. Examples of lower alkanoyl-groups are acetyl, propanoyl and butanoyl. Lower alkenylen means e.g. vinylen, propenylen and butenylen. Lower alkenyl and lower alkynyl means groups like ethylen, propylen, butylen, 2-methyl-propenyl, and ethinylen, propinylen, butinylen, pentinylen, 2-methyl-pentinylen etc. Lower alkenyloxy means allyloxy, vinyloxy, propenyloxy and the like. The expression cycloalkyl means a saturated cyclic hydrocarbon ring with 3 to 7 carbon atoms, e.g. cyclopropyl, cyclobutyl, cyclopentyl, cyclohexyl and cycloheptyl, which may be substituted with lower alkyl, hydroxy-lower alkyl, amino-lower alkyl, lower alkoxy-lower alkyl and lower alkenylen groups. The expression heterocyclyl means saturated or unsaturated (but not aromatic ) four, five-, six- or seven-membered rings containing one or two nitrogen, oxygen or sulfur atoms which may be the same or different and which rings may be adequatly substituted with lower alkyl, amino, nitro, hydroxy, lower alkoxy, e.g. piperidinyl, morpholinyl, thiomorpholinyl, piperazinyl, tetrahydropyranyl, dihydropyranyl, 1,4-dioxanyl, pyrrolidinyl, tetrahydrofuranyl, dihydropyrrolyl, dihydroimidazolyl, dihydropyrazolyl, pyrazolidinyl, 5-oxo-1,2,4-oxadiazolyl, 5-oxo-1,2,4-thiadiazolyl, 5-thioxo-1,2,4-oxadiazolyl, 2-oxo-1,2,3,5-oxathiadiazolyl etc. and substituted derivatives of such rings with substituents as outlined above. The expression heteroaryl means six-membered aromatic rings containing one to four nitrogen atoms, benzo-fused six-membered aromatic rings containing one to three nitrogen atoms, five-membered aromatic rings containing one oxygen or one nitrogen or one sulfur atom, benzo- fused five-membered aromatic rings containing one oxygen or one nitrogen or one sulfur atom, five membered aromatic rings containing an oxygen and nitrogen atom and benzo fused derivatives thereof, five membred aromatic rings containing a sulfur and a nitrogen atom and benzo fused derivatives thereof, five-membered aromatic rings containing two nitrogen atoms and benzo fused derivatives thereof, five membered aromatic rings containing three nitrogen atoms and benzo fused derivatives thereof or the tetrazolyl ring; e.g. furanyl, thienyl, pyrrolyl, pyridinyl, pyrimidinyl, indolyl, quinolinyl, isoquinolinyl, imidazolyl, triazinyl, thiazinyl, thiazolyl, isothiazolyl, pyridazinyl, oxazolyl, isoxazolyl, triazinyl, thiazinyl, thiazolyl, isothiazolyl, pyridazinyl, oxazolyl, isoxazolyl etc. whereby such rings may be substituted with lower alkyl, lower alkenyl, amino, amino-lower alkyl, halogen, hydroxy, lower alkoxy, trifluoromethoxy, trifluoromethyl, carboxyl, carboxamidyl, thioamidyl, amidinyl, lower alkyl-methanoylate, cyano, hydroxy-lower alkyl, lower alkyl-oxy-lower alkyl or another heteroaryl- (preferrably tetrazolyl) or heterocyclyl-ring (preferrably 5-oxo-1,2,4-oxadiazolyl, 5-oxo-1,2,4-triazolyl, 5-oxo-1,2,4-thiadiazolyl, 5-thioxo-1,2,4-oxadiazolyl or 2-oxo-1,2,3,5-oxathiadiazolyl). The expression aryl represents unsubstituted as well as mono-, di- or tri-substituted aromatic rings with 6 to 10 carbon atoms like phenyl or naphthyl rings which may be substituted with aryl, halogen, hydroxy, lower alkyl, lower alkenyl, lower alkynyl, lower alkoxy, lower alkenyloxy, lower alkynyl-lower alkyl-oxy, lower alkenylen, lower alkylenoxy, lower alkylenoxy or lower alkylendioxy forming with the phenyl ring a five- or six-membered ring, hydroxy-lower alkyl, hydroxy-lower alkenyl, hydroxy-lower alkyl-lower alkynyl, lower alkyloxy-lower alkyl, lower alkyloxy-lower alkyloxy, trifluoromethyl, trifluoromethoxy, cycloalkyl, hydroxy-cycloalkyl, heterocyclyl, heteroaryl.

In the compounds of the present invention, there are geometrical isomers such as cis- and trans-compounds [or (E)- and (Z)-compounds] possible due to double bonds present in the compounds covered by general formula I. The present invention covers each of the separated isomers [(E)- or (Z)-compound], as well as mixtures of both isomers in any ratio. In the present invention the compounds according to general formula I, in which the groups $R^5$ and $R^6$ are in trans-configuration are especially preferred.

Especially preferred compounds are compounds of general formula I wherein $R^3$ represents phenyl or mono-substituted phenyl substituted with lower alkyloxy, especially methoxy and X represents oxygen.

A second group of especially preferred compounds of general formula I are the compounds wherein $R^3$ represents phenyl or mono-substituted phenyl substituted with lower alkoxy, especially methoxy and X, Y and Z represent oxygen.

A third group of especially preferred compounds of general formula I are the compounds wherein $R^3$ represents phenyl or mono-substituted phenyl substituted with lower alkoxy, especially methoxy, X, Y and Z represent oxygen and Q represents —$(CH_2)_n$— with n=2 or 3.

A fourth group of especially preferred compounds of general formula I are the compounds wherein $R^3$ represents di-substituted phenyl substituted with one halogen and one lower alkoxy-group, especially one methoxy-group, X, Y and Z represent oxygen and Q represents—$(CH_2)_n$— with n=2 or 3.

A fifth group of especially preferred compounds of general formula I are the compounds wherein $R^3$ represents or mono- or di-substituted phenyl substituted with a chlorine atom and/or lower alkoxy, especially methoxy, X, Y and Z represent oxygen, Q represents —$(CH_2)_n$— with n=2 or 3 and $R^2$ represents heteroaryl.

The expression pharmaceutically acceptable salts encompasses either salts with inorganic acids or organic acids like hydrohalogenic acids, e.g. hydrochloric or hydrobromic acid; sulfuric acid, phosphoric acid, nitric acid, citric acid, formic acid, acetic acid, maleic acid, tartaric acid, methylsulfonic acid, p-toluolsulfonic acid and the like or in case the compound of formula I is acidic in nature with an inorganic base like an alkali or earth alkali base, e.g. sodium hydroxide, potassium hydroxide, calcium hydroxide etc.

The compounds of the general formula I might have one or more asymmetric carbon atoms and may be prepared in form of optically pure enantiomers or diastereomers, mixtures of enantiomers or diastereomers, diastereomeric racemates, mixtures of diastereomeric racemates and also in the meso-form. The present invention encompasses all these forms. Mixtures may be separated in a manner known per se, i.e. by column chromatography, thin layer chromatography, HPLC, crystallization etc.

Because of their ability to inhibit the endothelin binding, the described compounds of the general formula I and their pharmaceutically acceptable salts may be used for treatment of diseases which are associated with an increase in vasoconstriction, proliferation or inflammation due to endothelin. Examples of such diseases are hypertension, coronary diseases, cardiac insufficiency, renal and myocardial ischemia, renal failure, cerebral ischemia, dementia, migraine, subarachnoidal hemorrhage, Raynaud's syndrome, portal hypertension and pulmonary hypertension. They can also be used for treatment of atherosclerosis, prevention of restenosis after balloon or stent angioplasty, inflammation, stomach and duodenal ulcer, cancer, prostatic hypertrophy, erectile dysfunction, hearing loss, amaurosis, chronic bronchitis, asthma, gram negative septicemia, shock, sickle cell anemia, glomerulonephritis, renal colic, glaucoma, therapy and prophylaxis of diabetic complications, complications of vascular or cardiac surgery or after organ transplantation, complications of cyclosporin treatment, pain, as well as other diseases presently known to be related to endothelin.

These compositions may be administered in enteral or oral form e.g. as tablets, dragees, gelatine capsules, emulsions, solutions or suspensions, in nasal form like sprays or rectally in form of suppositories. These compounds may also be administered in intramuscular, parenteral or intravenous form, e.g. in form of injectable solutions.

These pharmaceutical compositions may contain the compounds of formula I as well as their pharmaceutically acceptable salts in combination with inorganic and/or organic excipients which are usual in the pharmaceutical industry like lactose, maize or derivatives thereof, talcum, stearinic acid or salts of these materials.

For gelatine capsules vegetable oils, waxes, fats, liquid or half-liquid polyols etc. may be used. For the preparation of solutions and sirups e.g. water, polyols, saccharose, glucose etc. are used. Injectables are prepared by using e.g. water, polyols, alcohols, glycerin, vegetable oils, lecithin, liposomes etc. Suppositories are prepared by using natural or hydrogenated oils, waxes, fatty acids (fats), liquid or half-liquid polyols etc.

The compositions may contain in addition preservatives, stabilisation improving substances, viscosity improving or regulating substances, solubility improving substances, sweeteners, dyes, taste improving compounds, salts to change the osmotic pressure, buffer, anti-oxidants etc.

The compounds of formula I may also be used in combination with one or more other therapeutically useful substances e.g. α- and β-blockers like phentolamine, phenoxybenzamine, atenolol, propranolol, timolol, metoprolol, carteolol etc.; Vasodilators like hydralazine, minoxidil, diazoxide, flosequinan etc.; Calcium-antagonists like diltiazem, nicardipine, nimodipine, verapamil, nifedipine etc.; ACE-inhibitors like cilazapril, captopril, enalapril, lisinopril etc.; Potassium activators like pinacidil etc.; Angiotensin II antagonists; Diuretics like hydrochlorothiazide, chlorothiazide, acetolamide, bumetanide, furosemide, metolazone, chlortalidone etc.; Sympatholitics like methyldopa, clonidine, guanabenz, reserpine etc.; and other therapeutics which serve to treat high blood pressure or any cardiac disorders.

The dosage may vary within wide limits but should be adapted to the specific situation. In general the dosage given daily in oral form should be between about 3 mg and about 3 g, preferably between about 10 mg and about 1 g, especially preferred between 5 mg and 300 mg, per adult with a body weight of about 70 kg. The dosage should be administered preferably in 1 to 3 doses per day which are of equal weight. As usual children should receive lower doses which are adapted to body weight and age.

Preferred compounds are compounds of formula II

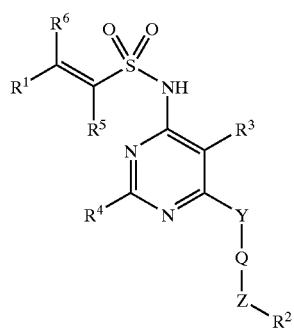

Formula II wherein $R^1$, $R^2$, $R^3$, $R^4$, $R^5$, $R^6$, Y, Q and Z are as defined in general formula I above,
and pharmaceutically acceptable salts of compounds of formula II.

Also preferred are compounds of formula III

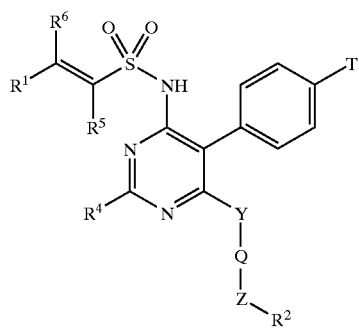

Formula III wherein $R^1$, $R^2$, $R^4$, $R^5$, $R^6$, Y, Q and Z are as defined in general formula I above and T represents a chlorine-, a bromine- or a hydrogen-atom or a methyl group or a methoxy group, and pharmaceutically acceptable salts of compounds of formula III.

Also preferred are compounds of formula IV

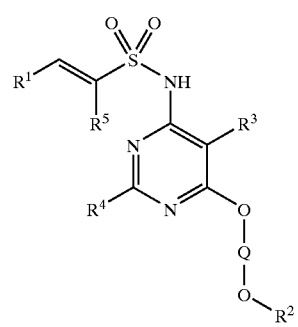

Formula IV wherein $R^1$, $R^2$, $R^3$, $R^4$ and Q are as defined in general formula I above, and pharmaceutically acceptable salts of compounds of formula IV.

Another especially preferred group of compounds are compounds of formula V

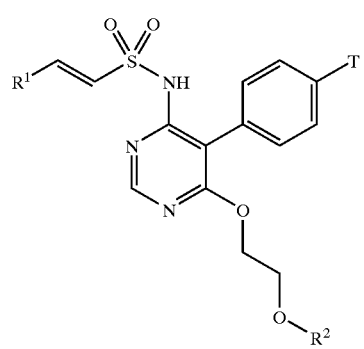

Formula V wherein $R^1$ and $R^2$ are as defined in general formula I above, and T represents a chlorine-, a bromine- or a hydrogen-atom or a methyl group or a methoxy group, and pharmaceutically acceptable salts thereof.

Especially preferred compounds among the group of compounds of formula V are those wherein $R^2$ represents heteroaryl.

Preferred compounds are:
2-Phenyl-ethenesulfonic acid [6-[2-(5-bromo-pyrimidin-2-yloxy)-ethoxy]-5-p-tolyl-pyrimidin-4-yl]-amide;
2-Phenyl-ethenesulfonic acid {5-(4-bromo-phenyl)-6-[2-(5-bromo-pyrimidin-2-yloxy)-ethoxy]-pyrimidin-4-yl}-amide;
2-Phenyl-ethenesulfonic acid {6-[2-(5-bromo-pyrimidin-2-yloxy)-ethoxy]-5-phenyl-pyrimidin-4-yl}-amide
2-Phenyl-ethenesulfonic acid {6-[2-(5-chloro-pyrimidin-2-yloxy)-ethoxy]-5-p-tolyl-pyrimidin-4-yl}-amide;
2-Phenyl-ethenesulfonic acid {6-[2-(4-bromo-phenoxy)-ethoxy]-5-p-tolyl-pyrimidin-4-yl}-amide;
2-Thiophen-3-yl-ethenesulfonic acid {6-[2-(5-bromo-pyrimidin-2-yloxy)-ethoxy]-5-p-tolyl-pyrimidin-4yl}-amide;
2-Thiophen-2-yl-ethenesulfonic acid {6-[2-(5-bromo-pyrimidin-2-yloxy)-ethoxy]-5-p-tolyl-pyrimidin-4-yl}-amide;
2-Thiophen-2-yl-ethenesulfonic acid {6-[2-(5-bromo-pyrimidin-2-yloxy)-ethoxy]-5-p-tolyl-[2,2']bipyrimidinyl-4-yl}-amide;
2-Phenyl-ethenesulfonic acid {6-[2-(5-bromo-pyrimidin-2-yloxy)-ethoxy]-5-p-tolyl-[2,2']bipyrimidinyl-4-yl}-amide;

2-Phenyl-ethenesulfonic acid [6-[2-(5-bromo-pyrimidin-2-yloxy)-ethoxy]-5-(2-methoxy-phenoxy)-pyrimidin-4-yl]-amide;
2-Phenyl-ethenesulfonic acid [6-[2-(5-bromo-pyrimidin-2-yloxy)-ethoxy]-5-(3-methoxy-phenoxy)-pyrimidin-4-yl]-amide;
2-Phenyl-ethenesulfonic acid [6-[2-(5-bromo-pyrimidin-2-yloxy)-ethoxy]-5-(2-methoxy-phenoxy)-2-pyrazin-2-yl-pyrimidin-4-yl]-amide;
2-Phenyl-ethenesulfonic acid [6-[2-(5-bromo-pyrimidin-2-yloxy)-ethoxy]-5-(2-methoxy-phenoxy)-2-morpholin-4-yl-pyrimidin-4yl-pyrimidin-4yl]-amide;
2-Phenyl-ethenesulfonic acid {5-(2-methoxy-phenoxy)-2-morpholin-4-yl-6-[2-(5-trifluoromethyl-pyrimidin-2-yloxy)-ethoxy]-prrimidin-4yl}-amide;
2-Phenyl-ethenesulfonic acid {5-(2-methoxy-phenoxy)-6-[2-(pyrimidin-2-yloxy)-ethoxy]-[2,2]bipyrimidinyl-4-yl}-amide;
2-Thiophen-2-yl-ethenesulfonic acid [6-[2-(5-bromo-pyrimidin-2-yloxy)-ethoxy]-5-(2-methoxy-phenoxy)-[2,2']bipyrimidinyl-4yl]-amide;
2-Thiophen-2-yl-ethenesulfonic acid [6-[2-(5-bromo-pyrimidin-2-yloxy)-ethoxy]-5-(2-methoxy-[phenoxy)-2-pyridin-4-yl-pyrimidin-4-yl]-amide;
2-Phenyl-ethenesulfonic acid [6-[2-(5-bromo-pyrimidin-2-yloxy)-ethoxy]-5-(2-chloro-5-methoxy-phenoxy)-pyrimidin-4-yl]-amide;

and pharmaceutically acceptable salts thereof.

Especially Preferred Compounds Are:

2-Phenyl-ethenesulfonic acid [6-[2-(5-bromo-pyrimidin-2-yloxy)-ethoxy]-5-(4-chloro-phenyl)-pyrimidin-4-yl]-amide;
2-Phenyl-ethenesulfonic acid {6-[2-(5-bromo-pyrimidin-2-yloxy)-ethoxy]-2-pyridin-4-yl-5-p-tolyl-pyrimidin-4-yl}-amide;

and pharmaceutically acceptable salts thereof.

Compounds of the general formula I of the present invention can be prepared according to the general sequence of reactions outlined below. For simplicity and clarity reasons sometimes only parts of the synthetic possibilities which lead to compounds of general formula I are described. The literature references given in brackets [ ] are set forth at the end of this paragraph.

Possibility A

The desired compounds of general formula I can be prepared by reacting a compound of the formula 1:

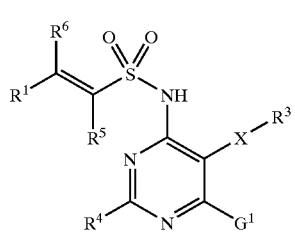

Formula 1 wherein $G^1$ is a reactive residue, preferentially a chloro atom, and the other symbols are as defined in general formula I above, with a compound of the formula 2:

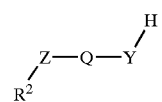

Formula 2 wherein the symbols are the same as defined in general formula I above, or a salt thereof.

Possibility B

The compounds of general formula I may also be prepared by reacting a compound of formula 3:

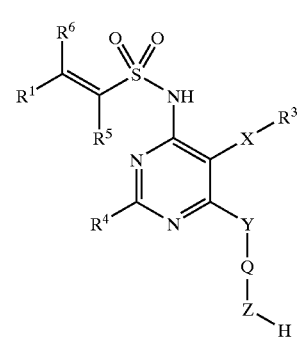

Formula 3 wherein the symbols are the same as defined in general formula I above, or a salt thereof, with a compound of the formula 4;

$$G^2—R^2$$

Formula 4 wherein $G^2$ is a reactive residue, preferentially a halogen atom, and the other symbol is the same as defined in general formula I above.

Possibility C

The compounds of general formula I may also be prepared by reacting a compound of the formula 5:

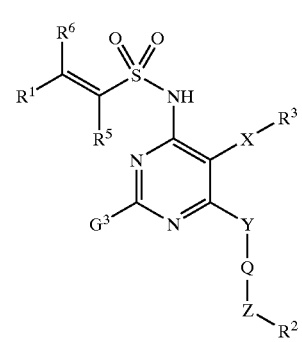

Formula 5

Wherein $G^3$ is a lower alkylsulfonyl group or a phenylsulfonyl group or a halogen atom, and the other symbols are the same as described in general formula I above, or a salt thereof, with a compound of the formula 6:

$$R^4—H$$

Formula 6 wherein $R^4$ is the same as defined in general formula I above, or a salt thereof.

For possibilities A to C see also [5]

Scheme 1

Preparation of the precursors 1 and 3, with X, Y and Z representing oxygen:

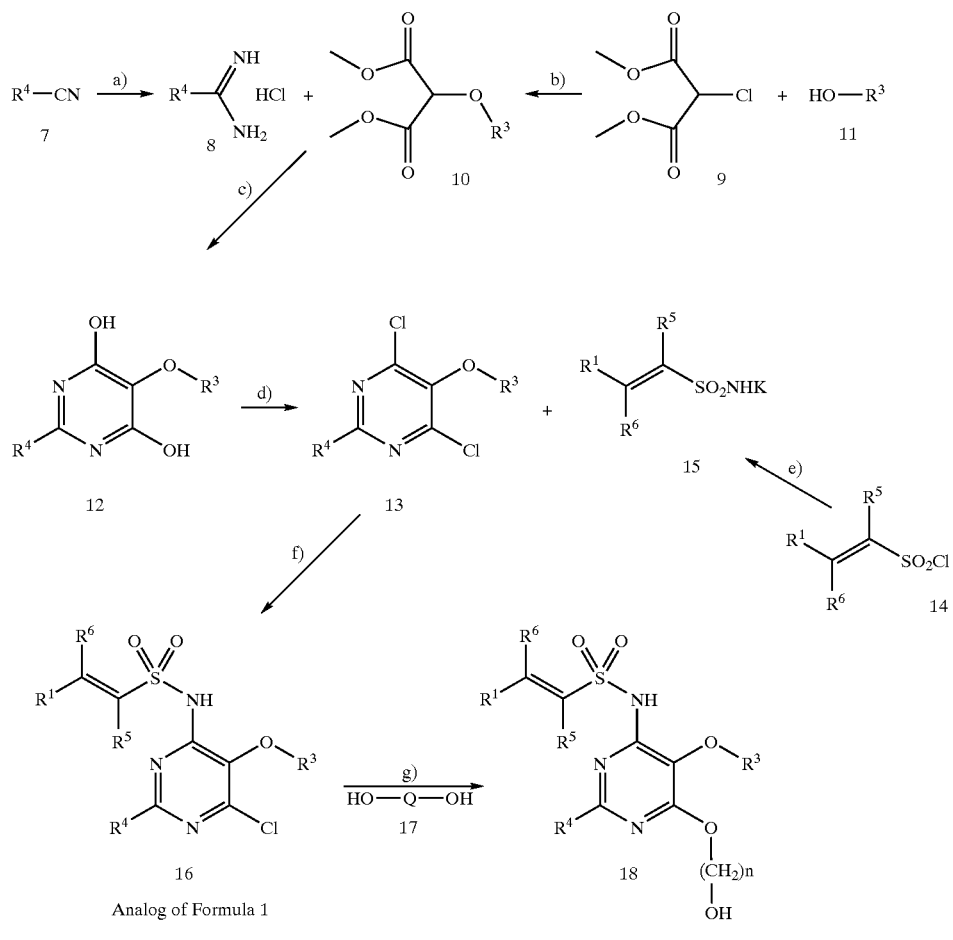

a) NaOMe, MeOH then NH$_4$Cl or LiN(Si(CH$_3$)$_3$)$_2$ then HCl/i-PrOH; b) K$_2$CO$_3$, acetone; c) NaOMe, MeOH; d) POCl$_3$; e) NH$_3$/THF then KOtBu, MeOH; f) DMSO; g) NaH, THF, DMF;

The amidines 8 were synthesized applying standard methodology [1] by reaction of the appropriate nitrile 7 either with sodium methylate in methanol followed by addition of ammonium chloride or by reaction with lithium hexamethyldisilazane followed by addition of hydrochloric acid in i-propanol. The 2-substituted malonic esters 10 were prepared according to published procedures [2] by reacting dimethylchloromalonate (9) with the appropriate alcohol 11 in acetone and potassium carbonate as base. The compounds 10 were dissolved in methanol and sodium methylate was added and stirring was continued for about 30 min followed by the addition of an amidine derivative 8. Stirring at ambient temperature was continued for another 8 h. After acidic work up the 4,6-dihydroxypyrimidines 12 could be isolated in yields of 70 to 90% [2]. Compounds 12 or the tautomeric form thereof were transformed into the dichloro derivatives 13 with phosphorous oxychloride in the presence of N,N-dimethylaniline at elevated temperatures (60–120° C.) in yields of 40 to 75% [3]. In some cases better yields were obtained by addition of PCl$_5$ or benzyltriethylammoniumchloride. The dichlorides 13 were reacted with an excess of the appropriate sulfonamide potassium salt 15 (prepared according to standard methodology from the sulfochlorides 14) in DMSO at room temperature to give the pyrimidines 16 in yields of 70 to 90% either after recrystallization from ethyl acetate/diethylether or chromatography through silica gel with ethyl acetate/heptane. The pyrimidine derivatives 16 are the central intermediates which can be transformed to the desired final products of general formula I either by applying procedures outlined under Possibility A or they can be transformed to the derivatives 18 by reaction with a di-hydroxy-compound represented by formula 17 in the presence of a base like sodium hydride in a solvent like THF at 50–80° C. and then transformed to final compounds according to the general formula I by applying procedures outlined under Possibility B above.

For further experimental descriptions see [1], [2], [3], [6].

The synthesis of compounds with X, Y or Z being another group than oxygen, can be carried out in analogous procedures.

Scheme 2

Preparation of the precursor 5, with X, Y, and Z representing Oxygen:

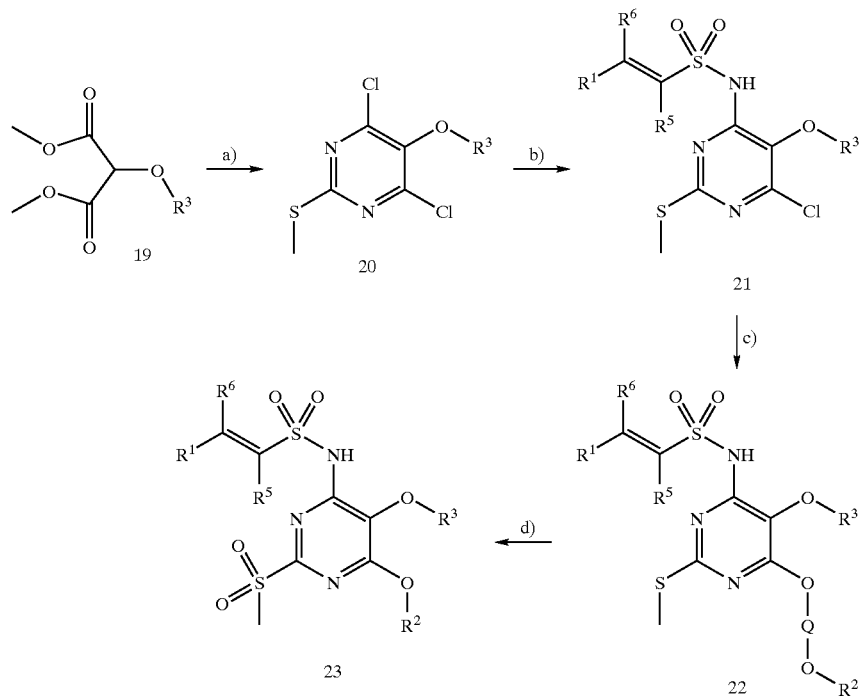

Analog of Formula 5 a) i) thiourea, NaOMe, MeOH, rt; ii) CH$_3$I, DMSO, rt; iii) POCl$_3$, dimethylaniline, 100–120° C.; b) (R$^1$)(R$^6$)C=C(R$^5$)SO$_2$—NHK, DMSO, rt;
c) R$^2$—O—Q—OH, NaH, THF/DMF, rt or 60–80° C. or HO—Q—OH, NaH, THF/DMF, rt or 60–80° C. followed by G$^2$—R$^2$, NaH, THF, 60–80° C.;
d) MCPBA, DCM, rt.

For further experimental descriptions see [1], [2], [3], [5], [6]. For the substitution of the sulfono-group, see especially [5]

The synthesis of compounds with X, Y or Z being another group than oxygen, can be carried out in analogous procedures.

Scheme 3

Preparation of the precursors for the synthesis of compounds of general formula I wherein X represents a bond [5]:

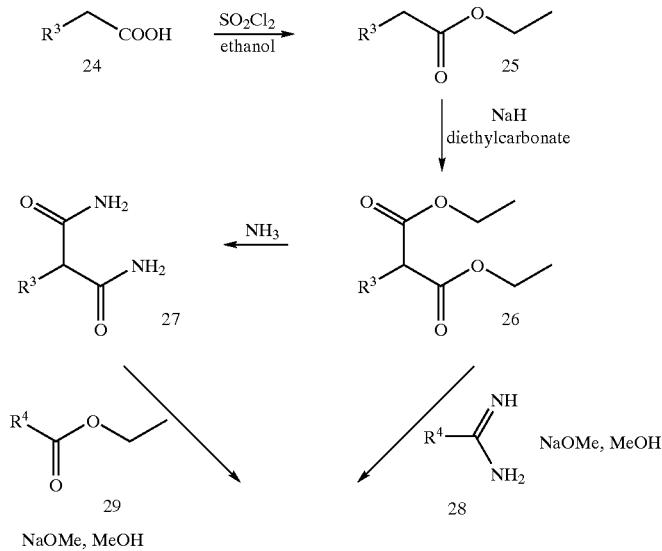

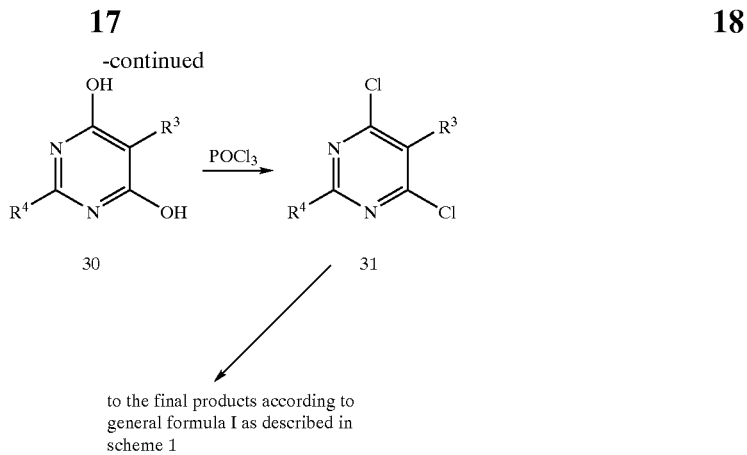

In the schemes 1 to 3 the symbols represent the same as defined in general formula I above.

Scheme 4: Preparation of Heteroaryl ethenylsulfonamides [11–13]

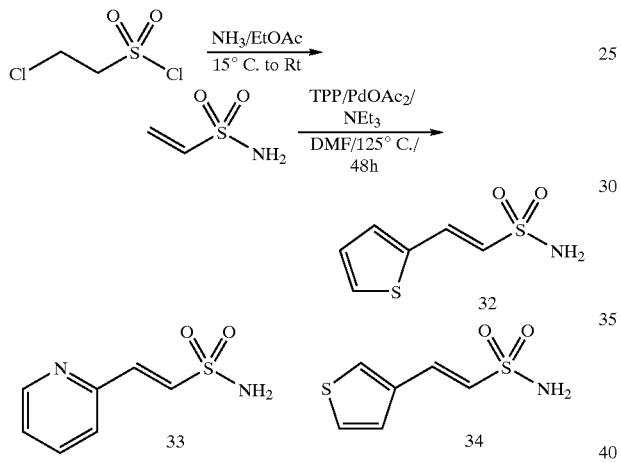

According to procedures described in the literature [11]–[13] the heteroaryl ethenylsufonamide derivatives 32 to 34 were prepared. The key step in this sequence is the palladium catalyzed coupling of vinylsulfonamide with the respective heteroaryl bromide. (In principle it is also possible to prepare the aryl ethenylsulfonamides via this procedure)

Scheme 5: Synthesis of substituted aryl ethenylsulfonamides [14–19]

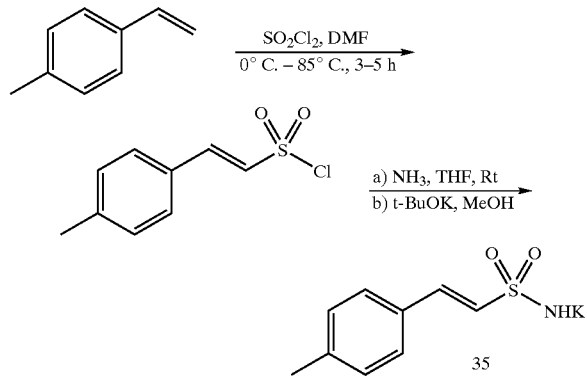

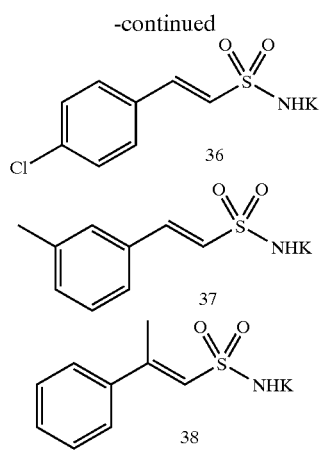

According to procedures described in the literature [14–19], the substituted aryl ethenyl sulfonamides 35 to 38 were prepared. Other derivatives could be prepared from the respective styrene precursors.

[1] W. Göhring, J. Schildknecht, M. Federspiel; *Chimia*, 1996, 50, 538–543.
[2] W. Neidhart, V. Breu, D. Bur, K. Burri, M. Clozel, G. Hirth, M. Müller, H. P. Wessel, H. Ramuz; *Chimia*, 1996, 50, 519–524 and references cited there.
[3] W. Neidhart, V. Breu, K. Burri, M. Clozel, G. Hirth, U. Klinkhammer, T. Giller, H. Ramuz; *Bioorg. Med. Chem. Lett.*, 1997, 7, 2223–2228. R. A. Nugent, S. T. Schlachter, M. J. Murphy, G. J. Cleek, T. J. Poel, D. G. Whishka, D. R. Graber, Y. Yagi, B. J. Keiser, R. A. Olmsted, L. A. Kopta, S. M. Swaney, S. M. Poppe, J. Morris, W. G. Tarpley, R. C. Thomas; *J. Med. Chem.*, 1998, 41, 3793–3803.
[4] J. March; *Advanced Organic Chemistry*, $4^{th}$ Ed., 1994, p. 499 and references cited there.
[5] EP 0 743 307 A1; EP 0 658 548 B1; EP 0 959 072 A1 (Tanabe Seiyaku)
[6] EP 0 633 259 B1; EP 0 526 708 A1; WO 96/19459 (F. Hoffmann-LaRoche)
[7] for the Synthesis of 5-membered heterocycles see: Y. Kohara et al; *J. Med. Chem.*, 1996, 39, 5228–5235 and references cited there.
[8] EP 0 882 719 A1 (Yamanouchi Pharmaceutical Co., Ltd).
[9] WO 00/52007 (F. Hoffmann-LaRoche AG).
[10] WO 00/42035 (F. Hoffmann-LaRoche AG).
[11] ????; *Bull. Soc. Chim. Fr.*; 1981, 71.
[12] ????; *J. Org. Chem.*; 1958, 23, 729.

[13] ????; *Bull. Chem. Soc. Jpn.;* 1991, 64, 1431.
[14] M. V. Ramana Reddy et al.; *Phosphorous, Sulfur and Silicon;* 1990, 53, 285–290.
[15] S. S. Arogba; *Organic Preparations and Procedures Int.,* 1991, 23(5), 639–643.
[16] D. Bhaskar Reddy et al.; *Phosphorous, Sulfur and Silicon;* 1993, 84, 63–71.
[17] M. Kameyama et al.; *Bull. Chem. Soc. Jpn.;* 1988, 61, 1231–1235.
[18] B. M. Culbertson et al.; *J. Chem. Soc. (C),* 1968, 992–993.
[19] D. Bhaskar Reddy et al.; *Indian J. Chem.;* 1995, 34B, 816–822.
[20] J. M. Fox, X. Huang, A. Chieffi, S. L. Buchwald; *J. Am. Chem. Soc.;* 2000, 122, 1360–1370.

REFERENTIAL EXAMPLES

Synthesis of Precursors

The following compounds were prepared according to the procedure described above and shown in Schemes 1 to 3. All compounds were characterized by 1 H-NMR (300 MHz) and occasionally by 13C-NMR (75 MHz) (Varian Oxford,) 300 MHz; chemical shifts are given in ppm relative to the solvent used; multiplicities: s=singlet, d=doublet, t=triplet; m=multiplet), by LC-MS (Waters Micromass; ZMD-platform with ESI-probe with Alliance 2790 HT; Colum: 2×30 mm, Gromsil ODS4, 3 μm, 120 A; Gradient: 0–100% acetonitril in water, 6 min, with 0.05% formic acid, flow: 0.45 ml/min; $t_R$ is given in min.), by TLC (TLC-plates from Merck, Silica gel 60 $F_{254}$) and occasionally by melting point.

The following Referential Examples illustrate the invention but do not at all limit the scope thereof. All temperatures are stated in ° C.

Referential Example 1

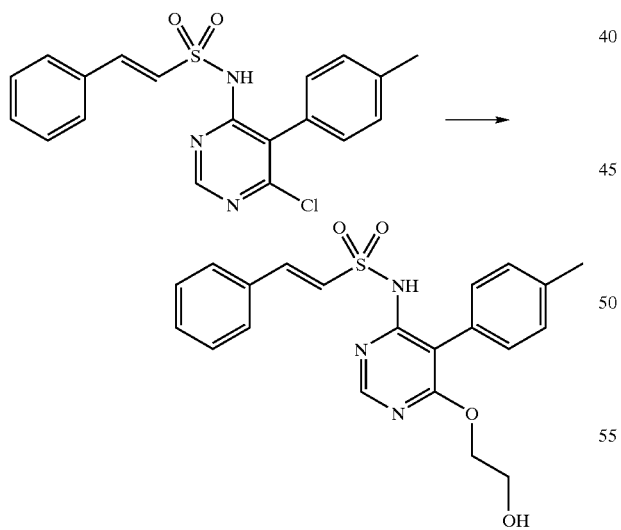

a) To a mixture of 1,2-dimethoxyethan (15 ml) and ethyleneglycol (40 ml) was added sodium (298 mg) in small portions. The mixture was stirred until the sodium was completely dissolved. Then DMF (15 ml), followed by 2-phenyl-ethenesulfonic acid(6-chloro-5-p-tolyl-pyrimidin-4-yl)-amide (1.0 g) was added. Stirring was continued for 4 days at 100° C. The mixture was evaporated and water (150 ml) was added to the residue followed by addition of acetic acid (1.0 ml). The precipitate was filtered off, washed with water and dried. The crude material was purified by chromatography over silicagel with EtOAc/methanol/aqueous ammonia (25%)=4/1/0.5 to give 2-phenyl-ethenesulfonic acid[6-(2-hydroxy-ethoxy)-5-p-tolyl-pyrimidin-4-yl]-amide (500 mg). $t_R$=4.54 (LC); $M^+$=412.38 (ES+).

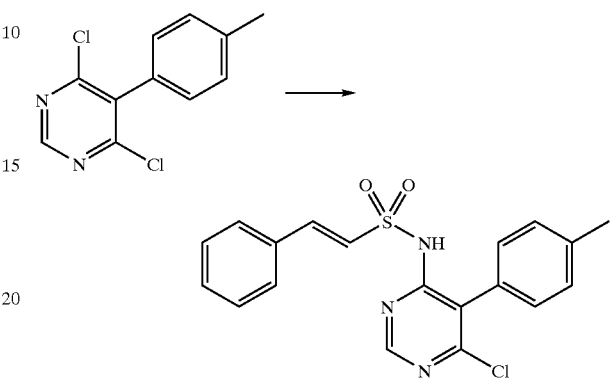

b) To 4,6-dichloro-5-p-tolyl-pyrimidine (2.0 g) disolved in DMSO (35 ml) was added di-isopropyl-ethyl-amine (1.46 ml) followed by 2-phenyl-ethenesulfonamide potassium salt (2.78 g). The mixture was stirred for 48 h at rt then poured onto water (500 ml) and diethylether (250 ml) was added and the solution was stirred for 30 minutes. The layers were separated and the water layer was acidified with acetic acid (2.0 ml) and cooled to 0° C. for 1 h. The precipitated product was filtered off and washed with water and diethylether and dried to give 2-phenyl-ethenesulfonic acid(6-chloro-5-p-tolyl-pyrimidin-4-yl)-amide (2.02 g). $t_R$=5.32 (LC); $M^+$=386.23 (ES+); $M^-$=384.22 (ES–).

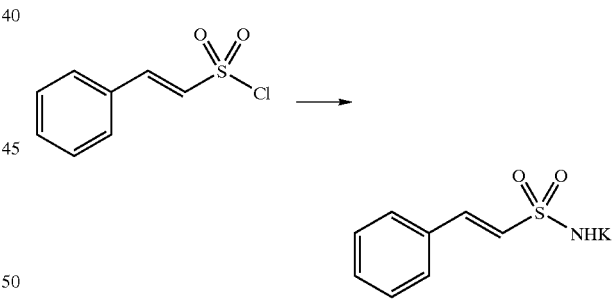

c) To 2-phenyl-ethenesulfonylchloride (10 g, commercially available from Aldrich) in THF (115 ml) was slowly added aqueous ammonia (25%) at 0° C. followed by stirring at rt for 30 min. The solvent was evaporated, the residue dissolved in EtOAc and washed with water (3×). The organic layer was dried over sodium sulfate, filtered and the solvent was evaporated. The residue was taken up in methanol (55 ml) and potassium tert.-butoxide (4.88 g) was added in portions. Stirring was continued for 30 min, the solvent was evaporated and the residue was dried to give 2-phenyl-ethenesulfonamide potassium salt (9.65 g). 1H-NMR (d6-DMSO): 7.7(m, 2H); 7.4(m, 3H); 7.3(d, 1 H); 7.2(d, 1H); 7.05(s, 2H, $NH_2$).

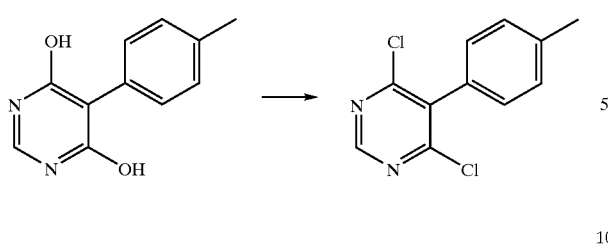

d) 5-p-tolyl-pyrimidine-4,6-diol (17.2 g) was dissolved in phosphorus oxy chloride (250 ml) and N,N-dimethylaniline (25 ml) was added. The mixture was stirred at 70° C. for 16 h, then concentrated in vacuo. The residue was poured onto ice-water and extracted with diethylether (3x). The combined organic extracts were washed with 1N hydrochloric acid and with saturated sodium chloride solution, dried over magnesium sulfate, filtered and the filtrate was evaporated. The crude brown material was recrystallized from i-propanol to give 4,6-dichloro-5-p-tolyl-pyrimidine (13.5 g). 1H-NMR (CDCl$_3$): 8.78(s, 1H); 7.35(d, 2H); 7.20(d, 2H); 2.41 (s, 3H).

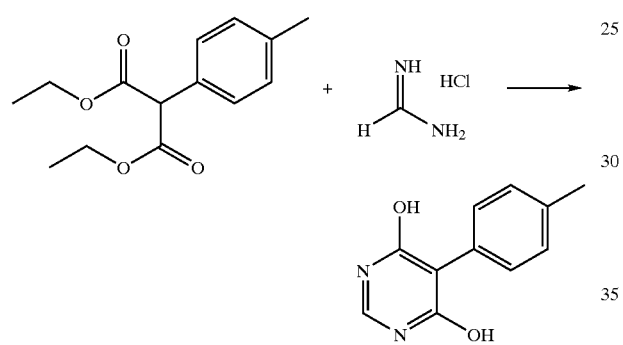

e) Sodium methylate (17 g) was dissolved in methanol (600 ml) at 0° C. 2-p-Tolyl-malonic acid diethyl ester (24.5 ml, commercially available from Aldrich), dissolved in 150 ml methanol, was added within 30 min. Stirring was continued for 1 h while slowly warming the mixture to rt. Formamidine hydrochloride (9.9 g, commercially available from Fluka) was added and stirring was continued for 16 h. The solvent was evaporated and 2 M hydrochloric acid (200 ml) was added to the residue followed by slow addition of 10 M sodium hydroxide to adjust the pH to 5. The precipitated product was filtered off and washed subsequently with water and diethylether and dried to give 5-p-tolyl-pyrimidine-4,6-diol (17.7 g). 1H-NMR (d6-DMSO): 8.0(s, 1H); 7.4(d, 2H); 7.1(d, 2H); 2.25(s, 3H).

Referential Example 2

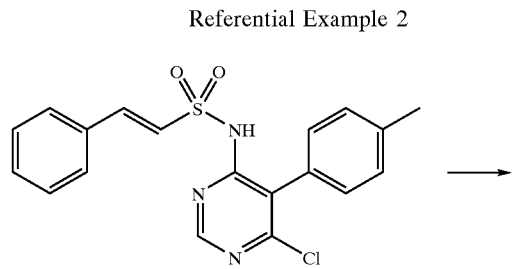

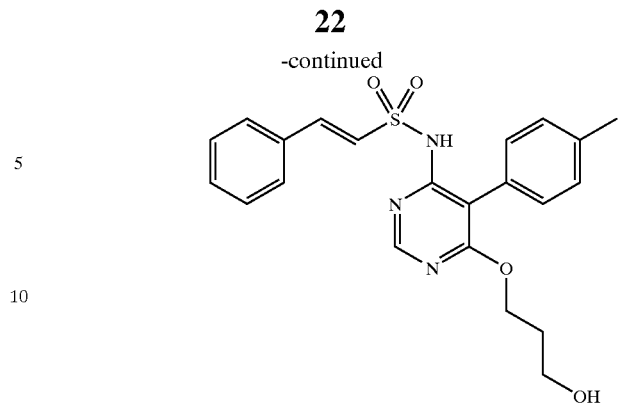

According to the procedure described in Referential Example 1a) 2-phenyl-ethenesulfonic acid [6-(3-hydroxy-propoxy)-5-p-tolyl-pyrimidin-4-yl]-amide was prepared. $t_R$=4.58 (LC); [M–H]$^+$=424.10 (ES–).

Referential Example 3

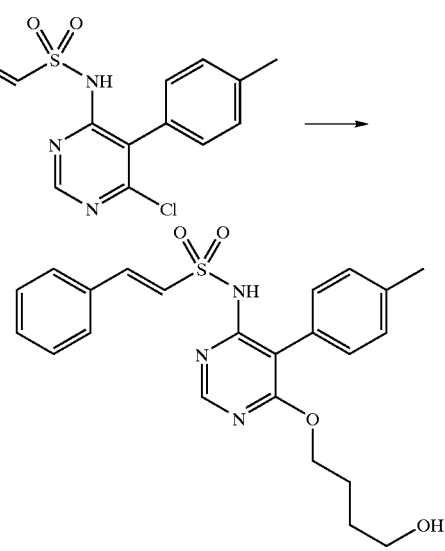

According to the procedure described in Referential Example 1a) 2-phenyl-ethenesulfonic acid [6-(4-hydroxy-butoxy)-5-p-tolyl-pyrimidin-4-yl]-amide was prepared. $t_R$=4.66 (LC); [M+H]$^+$=437.99 (ES+).

Referential Example 4

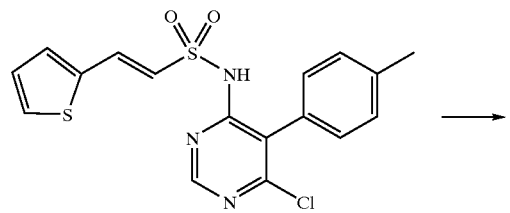

-continued

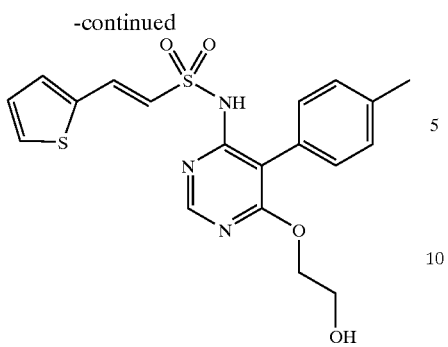

a) According to the procedure described in Referential Example 1a) 2-Thiophen-2-yl-ethenesulfonic acid [6-(2-hydroxy-ethoxy)-5-p-tolyl-pyrimidin-4-yl]-amide was prepared. $t_R$=4.36 (LC); [M+H]$^+$=418.15 (ES+).

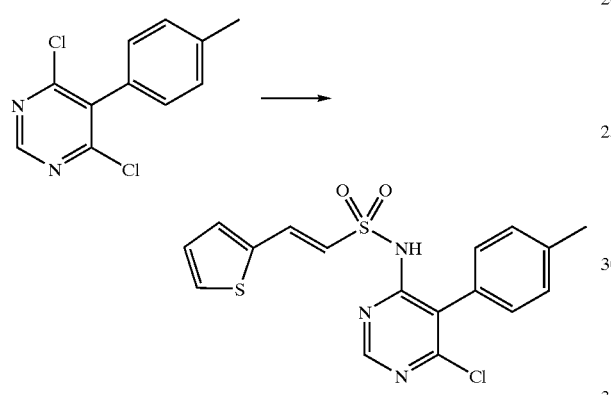

b) According to the procedure described in Referential Example 1b), 2-thiophen-2-yl-ethenesulfonic acid (6-chloro-5-p-tolyl-pyrimidin-4-yl)-amide was prepared from 4,6-dichloro-5-p-tolyl-pyrimidine and thiophen-2-yl-ethenesulfonic acid amide potassium salt. $t_R$=5.05 (LC); [M+H]$^+$=392.11 (ES+).

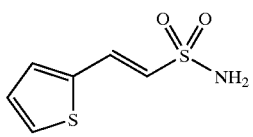

2-Thiophen-2-yl-ethenesulfonic acid amide was prepared according to procedures described in the literature [11], [12], [13].

Referential Example 5

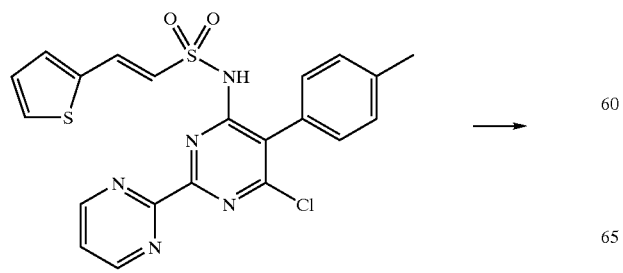

-continued

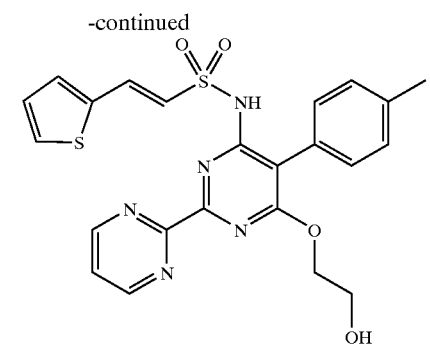

a) According to the procedure described in Referential Example 1a), 2-thiophen-2-yl-ethenesulfonic acid [6-(2-hydroxy-ethoxy)-5-p-tolyl-[2,2']bipyrimidinyl-4-yl]-amide was prepared. $t_R$=4.39 (LC); [M+H]$^+$=496.16 (ES+).

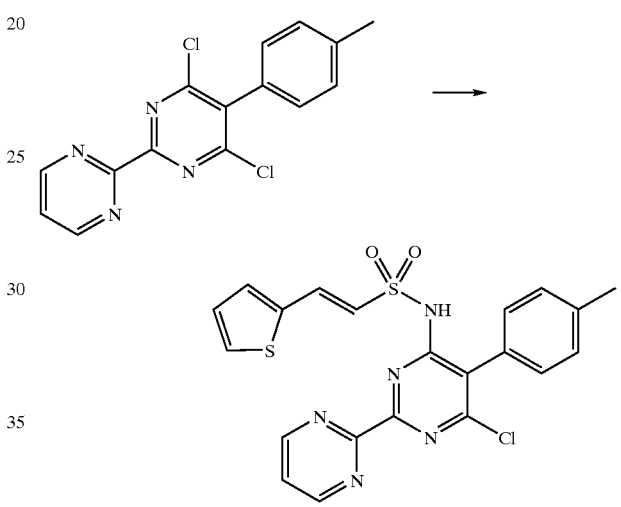

b) According to the procedure described in Referential Example 1b, 2-thiophen-2-yl-ethenesulfonic acid (6-chloro-5-p-tolyl-[2,2']bipyrimidinyl-4-yl)-amide was prepared from 4,6-dichloro-5-p-tolyl-[2,2']bipyrimidinyl and 2-thiophen-2-yl-ethenesulfonic acid amide potassium salt. $t_R$=4.84 (LC); [M+H]$^+$=470.00.

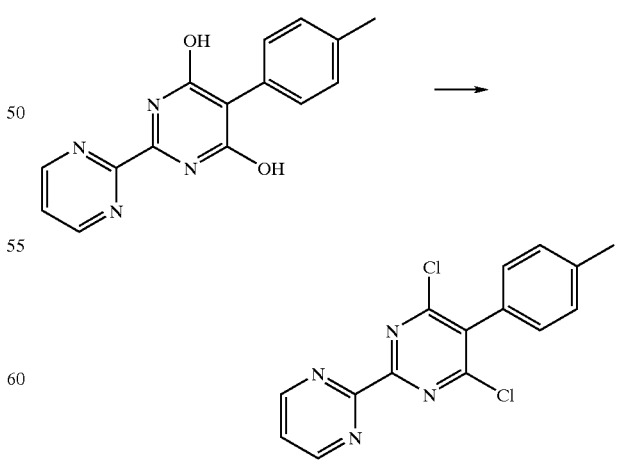

c) Accoridng to the procedure described in Referential Example 1c), 4,6-dichloro-5-p-tolyl-[2,2']bipyrimidinyl was prepared. $t^R$=4.42 (LC); [M+H]$^+$=317.08.

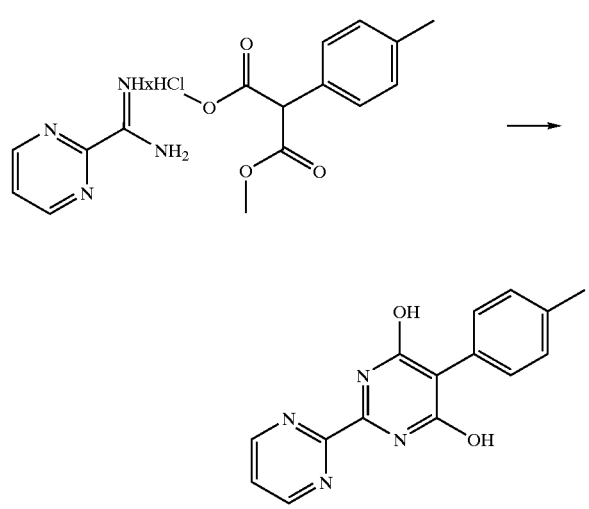

d) According to the procedure described in Referential Example 1d), 5-p-tolyl-[2,2']bipyrimidinyl-4,6-diol was prepared. $t_R$=3.38 (LC); [M+H]$^+$=281.08.

Referential Example 6

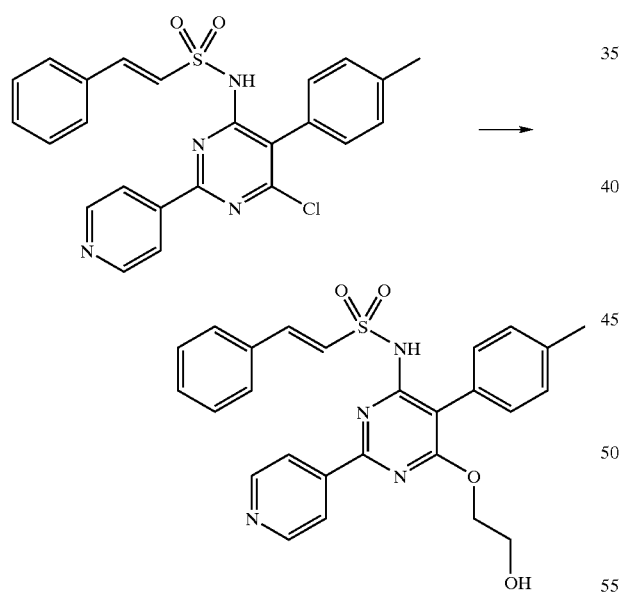

According to procedures described in the synthetic sequence in Referential Example 1a–e, by using isonicotinamidine hydrochloride instead of formamidine hydrochloride in the first step of the synthesis, 2-phenyl-ethenesulfonic acid [6-(2-hydroxy-ethoxy)-2-pyridin-4-yl-5-p-tolyl-pyrimidin-4-yl]-amide was prepared. $t_R$=4.36 (LC); [M+H]$^+$=489.39.

Referential Example 7

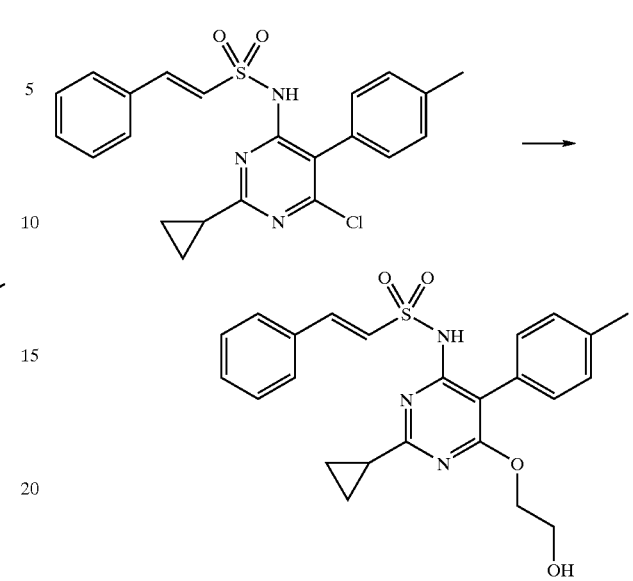

According to procedures described in the synthetic sequence in Referential Example 1a–e, by using cyclopropylformamidine hydrochloride instead of formamidine hydrochloride in the first step of the synthesis, 2-phenyl-ethenesulfonic acid-[2-cyclopropyl-6-(2-hydroxy-ethoxy)-5-p-tolyl-pyrimidin-4-yl]-amide was prepared. $t_R$=5.12 (LC); [M−H]$^+$=450.12 (ES−).

Referential Example 8

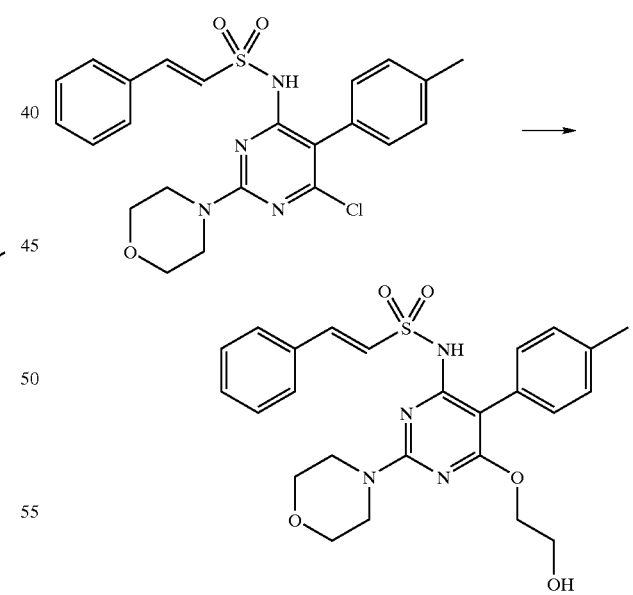

According to procedures described in the synthetic sequence in Referential Example 1a–e, by using morpholinoformamidine hydrochloride instead of formamidine hydrochloride in the first step of the synthesis, 2-phenyl-ethenesulfonic acid [6-(2-hydroxy-ethoxy)-2-morpholin-4-yl-5-p-tolyl-pyrimidin-4-yl]-amide was prepared. $t_R$=4.91 (LC); [M+H]$^+$=497.46 (ES+).

Referential Example 9

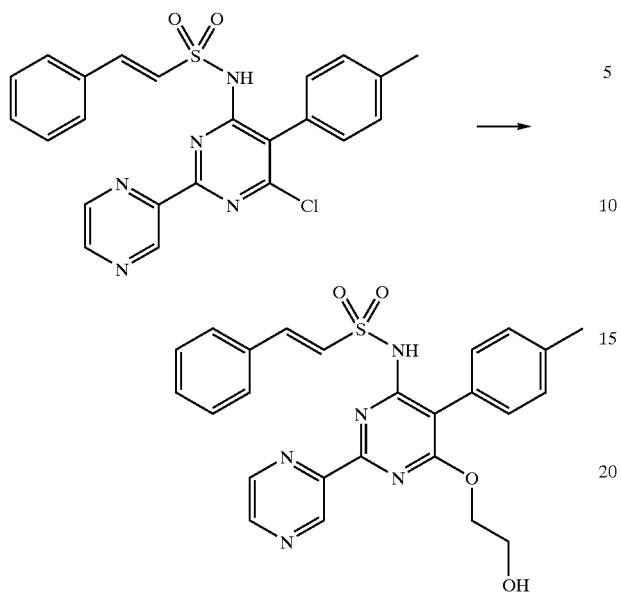

According to procedures described in the synthetic sequence in Referential Example 1a–e, by using pyrazinyl-formamidine hydrochloride instead of formamidine hydrochloride in the first step of the synthesis, 2-phenyl-ethenesulfonic acid [6-(2-hydroxy-ethoxy)-2-pyrazin-2-yl-5-p-tolyl-pyrimidin-4-yl]-amide was prepared. $t_R$=4.59 (LC); [M+H]$^+$=490.31 (ES+).

Referential Example 10

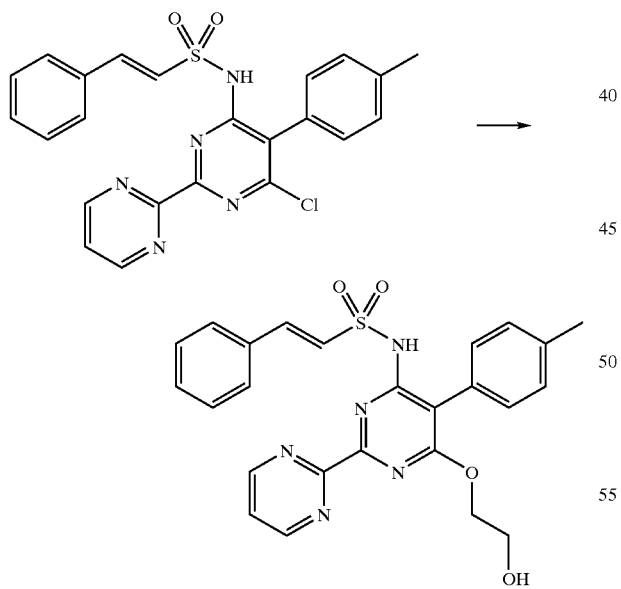

According to procedures described in the synthetic sequence in Referential Example 1 a–e, by using pyrimidin-2-yl-formamidine hydrochloride instead of formamidine hydrochloride in the first step of the synthesis, 2-phenyl-ethenesulfonic acid [6-(2-hydroxy-ethoxy)-5-p-tolyl-[2,2'] bipyrimidinyl-4-yl]-amide was prepared. $t_R$=4.51 (LC); [M+H]$^+$=490.34 (ES+).

Referential Example 11

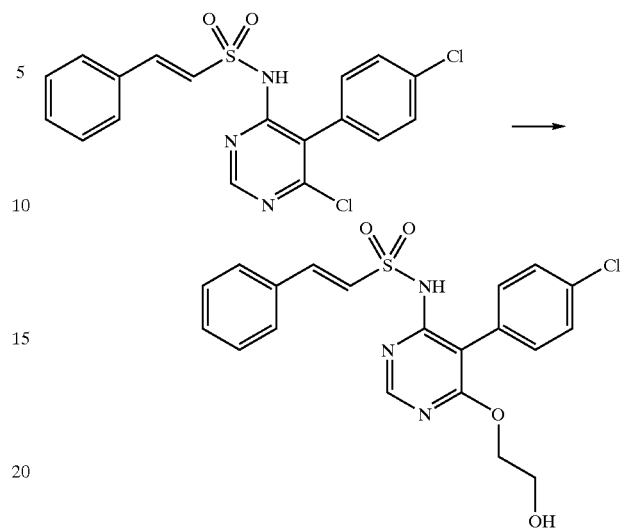

a) 6.20 g of 2-phenyl-ethenesulfonic acid [6-chloro-5-(4-chloro-phenyl)-pyrimidin-4-yl]-amide was added to a solution of 7.65 g of potassium-tert.-butylate in 100 ml of ethylene glycol. The resulting solution was heated to 110° C. and stirred for 17 h. The ethylene glycol was evaporated under high vacuum and the remaining residue was treated with 250 ml of cold water. The suspension was acidified by adding 10 g of citric acid monohydrate and stirred at 0° C. for 15 min. The precipitate was collected, washed with water and dried to give 6.71 g of 2-phenyl-ethenesulfonic acid [5-(4-chloro-phenyl)-6-(2-hydroxy-ethoxy)-pyrimidin-4-yl]-amide as a white powder. LC-MS: $t_R$=4.55 min, [M+H]$^+$=432.00 (ES+), [M–H]$^-$=429.98 (ES–).

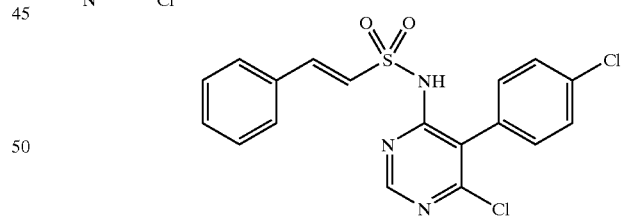

b) A solution of 6.50 g of 4,6-dichloro-5-(4-chlorophenyl)-pyrimidine and 9.43 g of 2-phenyl-ethenesulfonamide potassium salt (Referential Example 1c) in 50 ml of DMSO and 4.4 ml of diisopropyl-ethylamine was stirred at rt for 65 h. The mixture was diluted with 500 ml of water and 250 ml of diethyl ether and was vigorously stirred for 15 min. The suspension was acidified by adding 8.5 g of citric acid monohydrate and stirring was continued at 5° C. for 30 min. The precipitate was collected and washed with water. The crude product was crystallised from 2-propanol at 2–3° C. The crystals were collected, washed with cold 2-propanol and dried to give 6.23 g of 2-phenyl-ethenesulfonic acid [6-chloro-5-(4-chloro-phenyl)- pyrimidin-4-yl]-amide as a white powder. LC-MS: $t_R$=5.24 min, [M+H]⁺=405.89 (ES+), [M−H]⁻=403.92 (ES−).

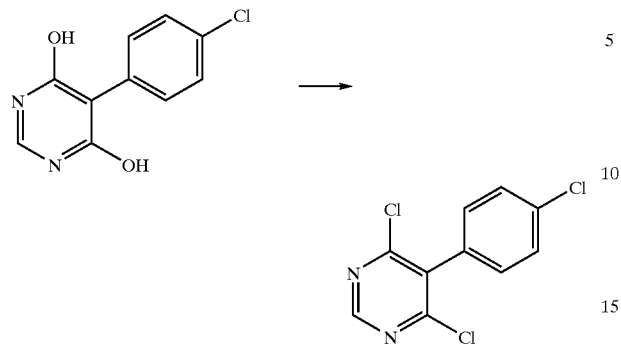

c) To a suspension of 16.44 g of 5-(4-chlorophenyl)-pyrimidine-4,6-diol in 165 ml of POCl₃ was carefully added 16.5 ml of N,N-dimethylaniline. The mixture was refluxed for 1.5 h. The dark green solution was evaporated and the residue was poured onto ice/water. The suspension was diluted with 200 ml 2 N HCl and water to about 1000 ml and stirred at 2° C. for 1 h. The precipitate was collected, washed with water and dried to give 18.66 g of 4,6-dichloro-5-(4-chlorophenyl)-pyrimidine as a slightly green powder.

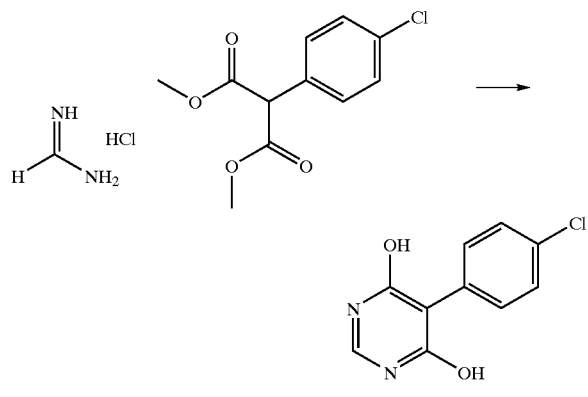

d) A solution of 18.90 g of 2-(4-chloro-phenyl)-malonic acid dimethyl ester in 200 ml of methanol was added dropwise at 0° C. to a solution of 14.60 g sodium methylate in 150 ml of methanol. The mixture was stirred for 1 h at 0° C. before 7.66 g of formamidine hydrochloride was added. The suspension was stirred at rt for 20 h. The solvent was removed and the residue was suspended in 200 ml 2 N aq. HCl. The pH of the suspension was carfully adjusted to 4–5 by adding 20 ml of 10 M NaOH, stirring was continued for 30 min. The white precipitate was collected, washed with water and diethyl ether and dried to give 16.44 g of 5-(4-chlorophenyl)-pyrimidine-4,6-diol as a white powder. LC-MS: $t_R$=2.75 min, [M+H]⁺=222.96 (ES+), [M−H]⁻=220.92 (ES−).

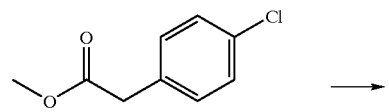

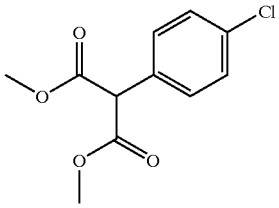

e) At 35° C. a solution of 52 g of 4-chlorophenylacetic acid methyl ester in 170 ml of THF was carefully added over a period of 70 min to a suspension of 15.6 g NaH in 550 ml of dry THF. Stirring was continued for 40 min without heating and the temperature dropped to 29° C. The evolution of gas had stopped before 94.8 ml of dimethylcarbonate was added dropwise while the temperature of the mixture was maintained at 25–28° C. After the evolution of gas had ceased, the mixture was diluted with 200 ml of THF and stirring was continued for 72 h at rt.

The mixture was carefully acidified with aq. HCl before bulk of the THF was removed in vacuo. The residue was dissolved in 1200 ml of diethyl ether, washed three times with 1 N aq. HCl and once with brine, dried over MgSO₄ and evaporated. The residue formed was collected, washed with diethyl ether and dried to give 42 g of 2-(4-chloro-phenyl)-malonic acid dimethyl ester as white crystals.

Referential Example 12

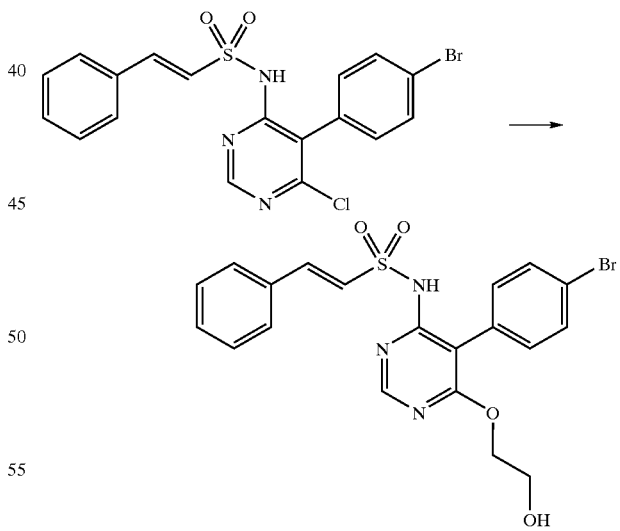

According to the procedures described in Referential Example 11a–e, by using 4-bromophenylacetic acid methyl ester as the initial starting material, 2-phenyl-ethenesulfonic acid [5-(4-bromo-phenyl)-6-(2-hydroxy-ethoxy)-pyrimidin-4-yl]-amide was obtained. LC-MS: $t_R$=4.57 min, [M+H]⁺= 478.05 (ES+).

Referential Example 13

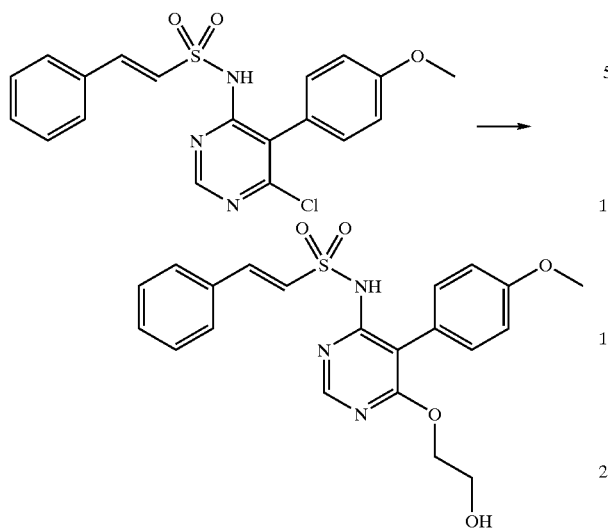

According to the procedures described in Referential Example 11a–e, by using 4-methoxyphenylacetic acid methyl ester as the initial starting material, 2-phenyl-ethenesulfonic acid [5-(4-methoxy-phenyl)-6-(2-hydroxy-ethoxy)-pyrimidin-4-yl]-amide was obtained. LC-MS: $t_R$=4.29 min, [M+H]$^+$=428.20 (ES+).

Referential Example 14

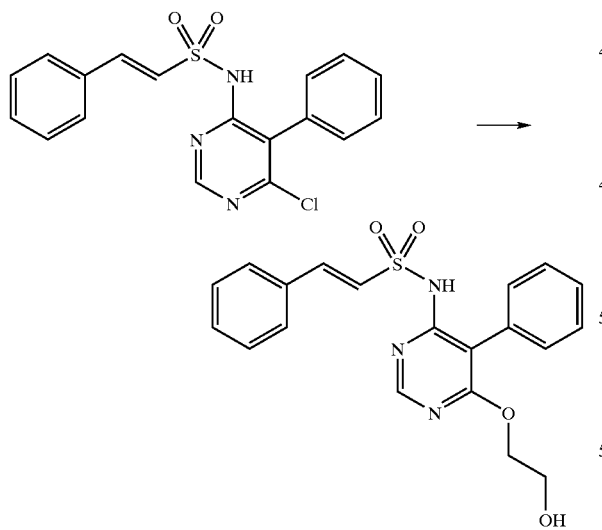

According to the procedures described in Referential Example 11a–d, by using diethyl phenylmalonate as the initial starting material, 2-phenyl-ethenesulfonic acid [5-phenyl-6-(2-hydroxy-ethoxy)-pyrimidin-4-yl]-amide was obtained. LC-MS: $t_R$=4.32 min, [M+H]$^+$=398.17 (ES+).

Referential Example 15

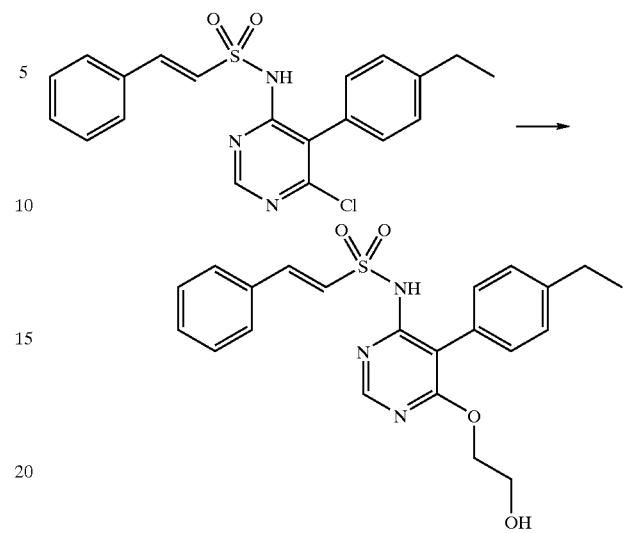

According to the procedures described in Referential Example 11a–d, by using 4-ethylphenylmalonic acid dimethylester, which can be prepared by methods described in [20], as the initial starting material, 2-phenyl-ethenesulfonic acid [5-(4-ethyl-phenyl)-6-(2-hydroxy-ethoxy)-pyrimidin-4-yl]-amide was obtained. LC-MS: $t_R$=4.68 min, [M+H]$^+$=426.07 (ES+).

Referential Example 16

The precursors depicted in Table 3 below can be prepared according to procedures published in the literature [1; 2; 3; 6; 9; 10] and according to methods described in Referential Examples 1 to 15.

TABLE 3

| Structure: | LC-MS: |
|---|---|
|  | $t_R$ = 5.11<br>[M + H]$^+$ = 484.40 |
|  | $t_R$ = 4.35<br>[M + H]$^+$ = 444.15 |

TABLE 3-continued

| Structure: | LC-MS: |
|---|---|
| | $t_R$ = 4.66<br>[M + H]$^+$ = 458.20 |
| | $t_R$ = 4.53<br>[M + H]$^+$ = 478.14 |
| | $t_R$ = 4.13<br>[M + H]$^+$ = 521.08 |
| | $t_R$ = 4.38<br>[M + H]$^+$ = 522.40 |
| | $t_R$ = 4.71<br>[M + H]$^+$ = 529.19 |

TABLE 3-continued

| Structure: | LC-MS: |
|---|---|
| | $t_R$ = 5.21<br>[M + H]$^+$ = 564.13 |
| | $t_R$ = 4.53<br>[M + H]$^+$ = 522.30 |

EXAMPLES

The following examples illustrate the invention but do not at all limit the scope thereof. All temperatures are stated in ° C. Reactions were checked by TLC and LC-MS. Reaction times can vary from 1 h to several days and reaction temperatures can vary from 20° C. to reflux temperature of THF.

Example 1

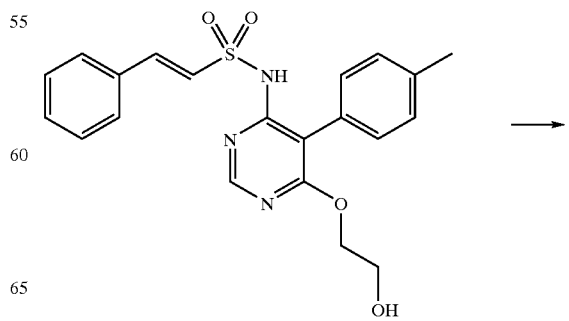

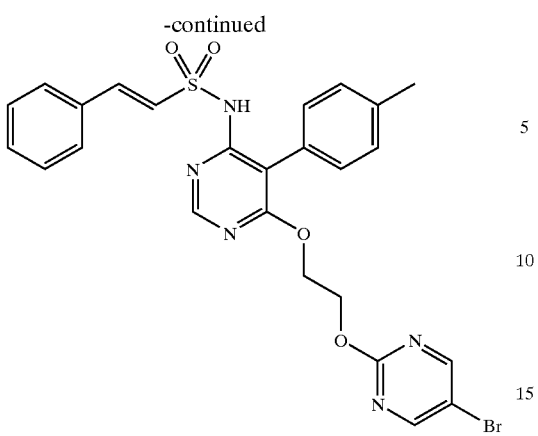

To sodium hydride (220 mg, 55–65% in mineral oil) was added THF (35 ml) followed by addition of 2-phenyl-ethenesulfonic acid [6-(2-hydroxy-ethoxy)-5-p-tolyl-pyrimidin-4-yl]-amide (250 mg). The mixture was stirred for 1 h at rt. Then 5-bromo-2-chloro-pyrimidine (188 mg) was added and stirring continued for 21 h at 80° C. The solvent was evaporated and diethylether (20 ml) was added to the residue. The precipitate was filtered off and washed with diethylether, dissolved in water and acidified by citric acid. The precipitate was filtered off and the crude material was purified by chromatography over silicagel with hexane/EtOAc=1/1 to give 2-phenyl-ethenesulfonic acid {6-[2-(5-bromo-pyrimidin-2-yloxy)-ethoxy]-5-p-tolyl-pyrimidin-4-yl}-amide (91 mg); $t_R$=5.39 (LC); $[M+H]^+$=570.34 (ES+); $[M-H]^-$=568.45 (ES−).

Example 2

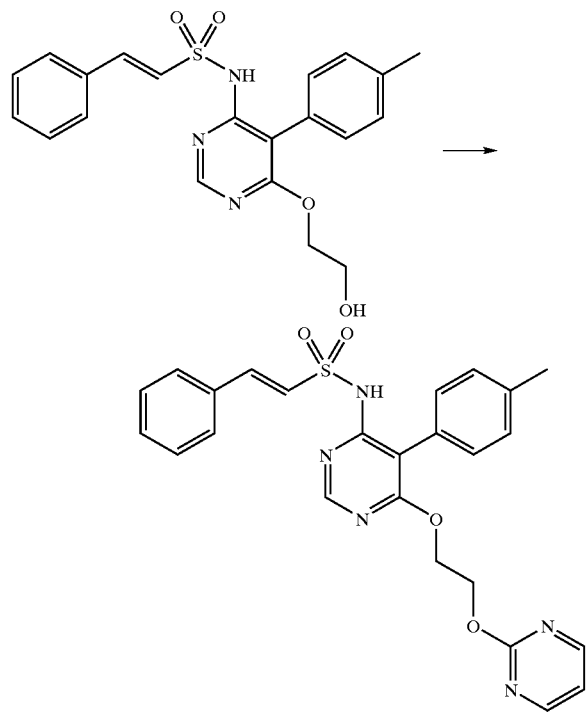

To sodium hydride (26 mg, 55–65% in mineral oil) was added THF (10 ml) followed by the addition of 2-phenyl-ethenesulfonic acid [6-(2-hydroxy-ethoxy)-5-p-tolyl-pyrimidin-4-yl]-amide (100 mg). The mixture was stirred for 1 h at rt. Then 2-chloro-pyrimidine (46 mg) was added and stirring continued for 19 h at 80° C. The solvent was evaporated and diethylether (20 ml) was added to the residue. The precipitate was filtered off and washed with diethylether, dissolved in water and acidified by citric acid. The precipitate was filtered off and the crude material was purified by chromatography over silicagel with hexane/EtOAc=1/1 to give 2-phenyl-ethenesulfonic acid {6-[2-(pyrimidin-2-yloxy)-ethoxy]-5-p-tolyl-pyrimidin-4-yl}-amide (23.7 mg); $t_R$=4.85 (LC); $[M+H]^+$=490.27 (ES+).

Example 3

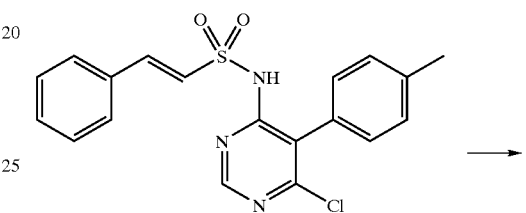

Ethyleneglycol-mono-(4-bromo-phenyl)-ether (112 mg) was dissolved in 1,2-dimethoxyethane (5 ml) and potassium tert.-butoxide (50 mg) was added and stirring continued for 1 h, followed by the addition of 2-phenyl-ethenesulfonic acid [6-chloro-5-p-tolyl-pyrimidin-4-yl]-amide (100 mg) and stirring was continued at 80° C. for 24 h. The reaction mixture was evaporated to dryness, water (20 ml) was added followed by acidification with 10% citiric acid and extraction with ethyl acetate (2×, 20 ml). The combined organic layers were dried over sodium sulfate and the solvent was evaporated. The crude product was recrystallized from 2-propanol and 2-phenyl-ethenesulfonic acid {6-[2-(4-bromo-phenoxy)-ethoxy]-5-p-tolyl-pyrimidin-4-yl}-amide (90 mg) was obtained as a white powder; $t_R$=6.12 (LC); $[M-H]^+$=565.75 (ES−).

Example 4

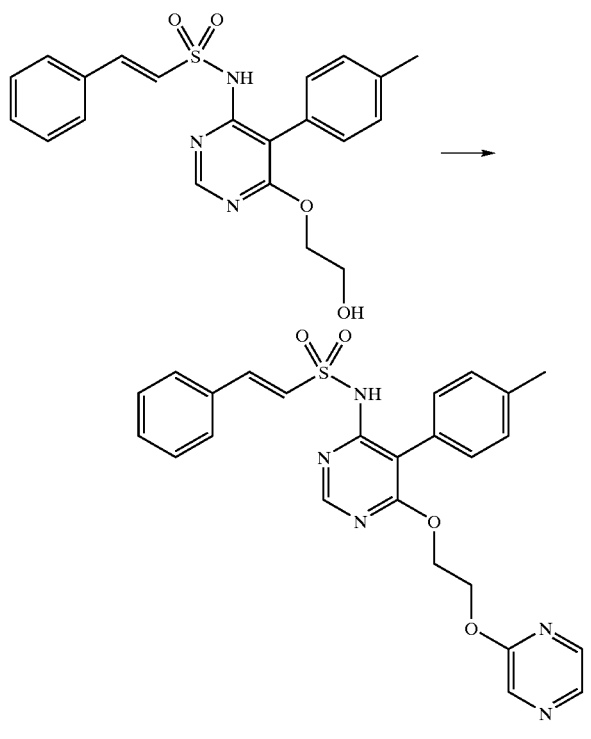

Example 5

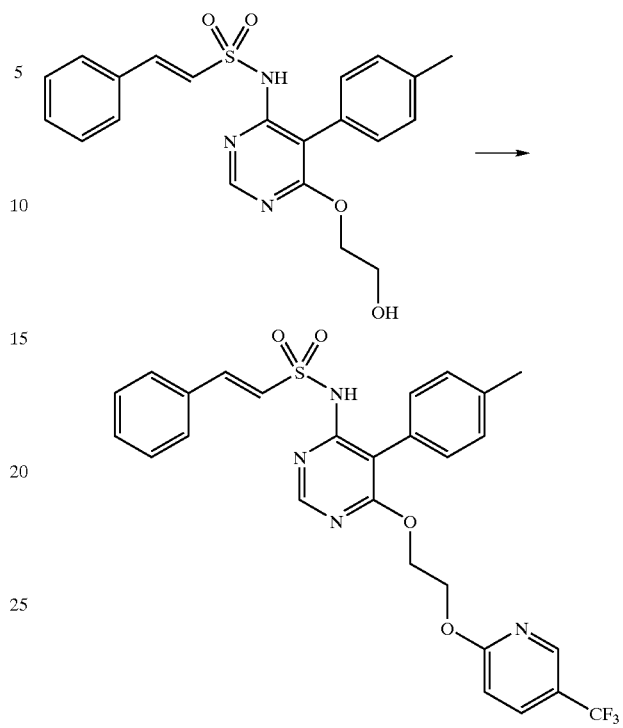

To sodium hydride (65 mg, 55–65% in mineral oil) was added THF (35 ml) followed by the addition of 2-phenyl-ethenesulfonic acid [6-(2-hydroxy-ethoxy)-5-p-tolyl-pyrimidin-4-yl]-amide (200 mg). The mixture was stirred for 1 h at rt. Then 2-chloro-pyrazine (114 mg) was added and stirring continued for 18 h at 80° C. The solvent was evaporated and diethylether (20 ml) was added to the residue. The precipitate was filtered off and washed with diethylether, dissolved in water, acidified by citric acid and extracted with ethyl acetate. The combined organic layers were dried over magnesium sulfate and concentrated in vacuo and the crude material was purified by chromatography over silicagel with hexane/EtOAc=1/1 to give 2-phenyl-ethenesulfonic acid {6-[2-)pyrazin-2-yloxy)-ethoxy]-5-p-tolyl-pyrimidin-4-yl}-amide (86.5 mg); $t_R$=5.13 (LC); [M+H]$^+$=490.21 (ES+).

2-Phenyl-ethenesulfonic acid [6-(2-hydroxy-ethoxy)-5-p-tolyl-pyrimidin-4-yl]-amide (150 mg) was dissolved in THF (10 ml) and sodium hydride (45 mg; 55–65% in mineral oil) was added. The mixture was stirred for 15 min at rt., followed by the addition of DMF (2 ml) and 2-chloro-5-trifluoromethyl-pyridine (146 mg) and heating to 75° C. for 5 h. Then the reaction mixture was evaporated to dryness and water (15 ml) and citric acid was added. The precipitated product was filtered off, washed with water and dried. 2-Phenyl-ethenesulfonic acid {5-p-tolyl-6-[2-(5-trifluoromethyl-pyridin-2-yloxy)-ethoxy]-pyrimidin-4-yl}-amide (130 mg) could be obtained as a white powder. $t_R$=5.92 (LC); [M+H]$^+$=557.38 (ES+).

Examples 6–240

The corresponding starting materials are treated in a manner according to the procedures given in examples 1–5 to give the compounds as listed in Tables 4–45.

TABLE 4

:Prep. according to Ex:

| Ex. No. | R$^1$ | R$^2$ | LC-MS | # |
|---|---|---|---|---|
| 6 | (styryl) | (4-chlorophenyl) | O(CH$_2$)$_2$ $t_R$ = 6.04<br>[M + H]$^+$:523.22 | 3 |

TABLE 4-continued
:Prep. according to Ex:
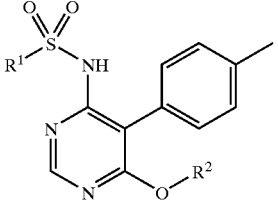
| Ex. No. | R¹ | R² | LC-MS | # |
|---|---|---|---|---|
| 7 | 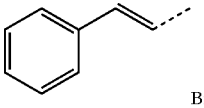 | 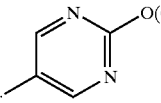 | $t_R$ = 5.55<br>[M + H]⁺:584.11 | 1 |
| 8 | 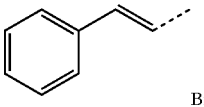 | 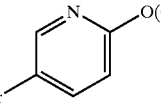 | $t_R$ = 6.12<br>[M + H]⁺:582.11 | 5 |
| 9 | 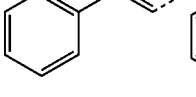 | 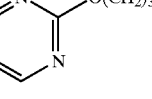 | $t_R$ = 5.07<br>[M + H]⁺:504.20 | 1 |
| 10 | 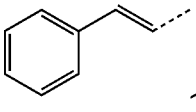 | 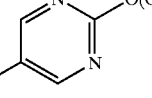 | $t_R$ = 5.22<br>[M + H]⁺:516.14 | 1 |
| 11 | 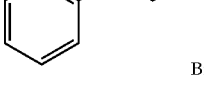 | 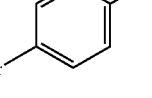 | $t_R$ = 5.92<br>[M + H]⁺:569.18 | 5 |
| 12 | 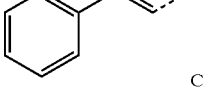 | 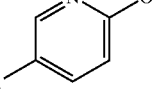 | $t_R$ = 5.84<br>[M + H]⁺:523.22 | 5 |
TABLE 5
: Prep. according to Ex:
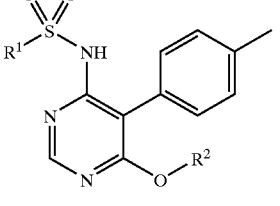
| Ex. No. | R¹ | R² | LC-MS | # |
|---|---|---|---|---|
| 13 | 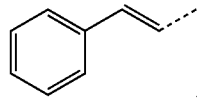 | 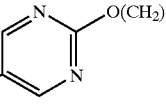 | $t_R$ = 5.14<br>[M + H]⁺:502.14 | 1 |

TABLE 5-continued

: Prep. according to Ex:

[Structure: R¹-SO₂-NH-pyrimidine with 4-methylphenyl and O-R²]

| Ex. No. | R¹ | R² | LC-MS | # |
|---|---|---|---|---|
| 14 | styryl | 5-chloropyrimidin-2-yl-O(CH₂)₂ | $t_R$ = 5.39 [M + H]⁺:524.23 | 1 |
| 15 | styryl | 5-fluoropyrimidin-2-yl-O(CH₂)₂ | $t_R$ = 5.16 [M + H]⁺:508.23 | 1 |
| 16 | styryl | benzoxazol-2-yl-O(CH₂)₂ | $t_R$ = 5.53 [M + H]⁺:529.39 | 1 |
| 17 | styryl | thiazol-2-yl-O(CH₂)₂ | $t_R$ = 5.29 [M + M]⁺:495.29 | 1 |
| 18 | styryl | benzothiazol-2-yl-O(CH₂)₂ | $t_R$ = 5.01 [M + H]⁺:545.24 | 1 |
| 19 | styryl | pyrimidin-2-yl-O(CH₂)₄ | $t_R$ = 5.17 [M + H]⁺:518.21 | 1 |

TABLE 6

: Prep. according to Ex:

[Structure: R¹-SO₂-NH-pyrimidine with 4-methylphenyl and O-R²]

| Ex. No. | R¹ | R² | LC-MS | # |
|---|---|---|---|---|
| 20 | styryl | 5-bromopyrimidin-2-yl-O(CH₂)₄ | $t_R$ = 5.75 [M + H]⁺:598.12 | 1 |

TABLE 6-continued
: Prep. according to Ex:
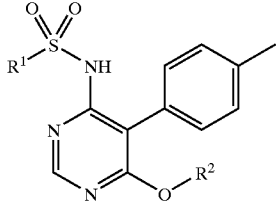
| Ex. No. | R¹ | R² | LC-MS | # |
|---|---|---|---|---|
| 21 | 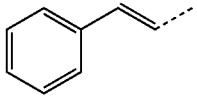 | 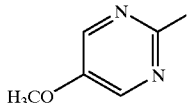 | $t_R$ = 5.12<br>[M + H]⁺:520.03 | 1 |
| 22 | 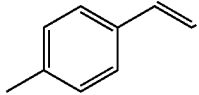 | 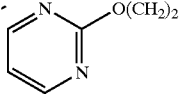 | $t_R$ = 5.09<br>[M + H]⁺:504.23 | 1 |
| 23 | 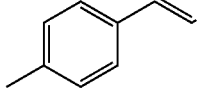 | 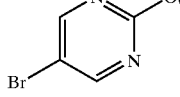 | $t_R$ = 5.60<br>[M + H]⁺:584.01 | 1 |
| 24 | 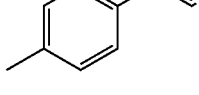 | 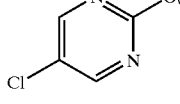 | $t_R$ = 5.53<br>[M + H]⁺:539.53 | 1 |
| 25 | 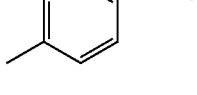 | 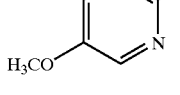 | $t_R$ = 5.26<br>[M + H]⁺:534.21 | 1 |
| 26 | 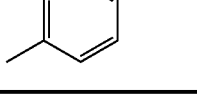 | 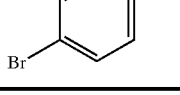 | $t_R$ = 6.03<br>[M + H]⁺:583.41 | 5 |
TABLE 7
: Prep. according to Ex:
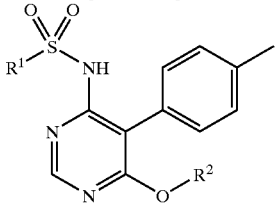
| Ex. No. | R¹ | R² | LC-MS | # |
|---|---|---|---|---|
| 27 | 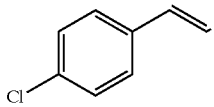 | 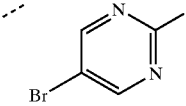 | $t_R$ = 5.63<br>[M + H]⁺:604.31 | 1 |

TABLE 7-continued
: Prep. according to Ex:
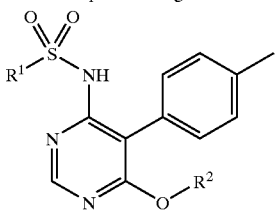
| Ex. No. | R¹ | R² | LC-MS | # |
|---|---|---|---|---|
| 28 | 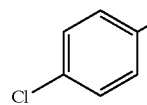 | 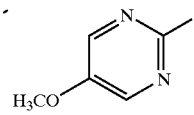 | $t_R$ = 5.30<br>[M + H]⁺:556.44 | 1 |
| 29 | 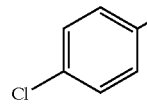 | 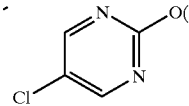 | $t_R$ = 5.57<br>[M + H]⁺:559.46 | 1 |
| 30 | 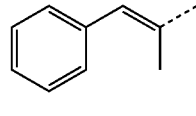 | 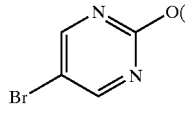 | $t_R$ = 5.47<br>[M + H]⁺:584.39 | 1 |
| 31 | 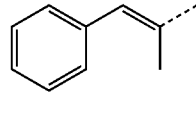 | 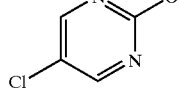 | $t_R$ = 5.43<br>[M + H]⁺:540.54 | 1 |
| 32 | 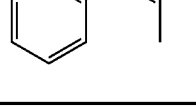 | 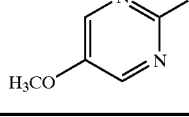 | $t_R$ = 5.13<br>[M + H]⁺:534.15 | 1 |
TABLE 8
: Prep. according to Ex:
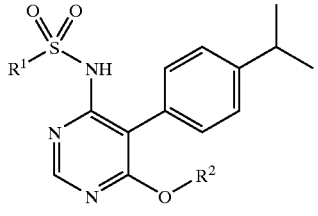
| Ex. No. | R¹ | R² | LC-MS | 1# |
|---|---|---|---|---|
| 33 | 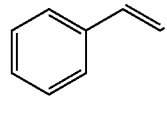 | 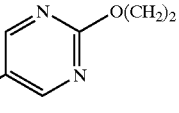 | $t_R$ = 6.02<br>[M + H]⁺:598.41 | 1 |
| 34 | 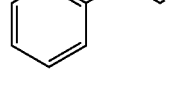 | 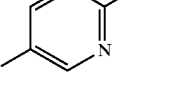 | $t_R$ = 5.63<br>[M + H]⁺:548.26 | 1 |

TABLE 8-continued

| 35 | PhCH=CH– | 2-O(CH2)2-(5-Cl-pyrimidin-4-yl) | $t_R$ = 5.96 [M + H]$^+$:553.57 | 1 |

(structure: R¹SO2NH-pyrimidine with 4-ethylphenyl and OR²)

| 36 | PhCH=CH– | 2-O(CH2)2-(5-Br-pyrimidin-4-yl) | $t_R$ = 5.64 [M + H]$^+$:583.47 | 1 |
| 37 | PhCH=CH– | 2-O(CH2)2-(5-H3CO-pyrimidin-4-yl) | $t_R$ = 5.27 [M + H]$^+$:534.19 | 1 |
| 38 | PhCH=CH– | 2-O(CH2)2-(5-Cl-pyrimidin-4-yl) | $t_R$ = 5.59 [M + H]$^+$:536.33 | 1 |

TABLE 9

: Prep. according to Ex:

(structure: R¹SO2NH-pyrimidine with 3,4-dimethylphenyl and OR²)

| Ex. No. | R¹ | R² | LC-MS | # |
| 39 | PhCH=CH– | 2-O(CH2)2-(5-H3CO-pyrimidin-4-yl) | $t_R$ = 5.27 [M + H]$^+$:534.18 | 1 |
| 40 | PhCH=CH– | 2-O(CH2)2-(5-Br-pyrimidin-4-yl) | $t_R$ = 5.65 [M + H]$^+$:584.30 | 1 |

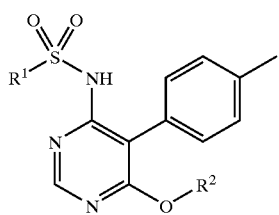

TABLE 9-continued
| Ex. No. | R¹ | R² | LC-MS | # |
|---|---|---|---|---|
| 41 | 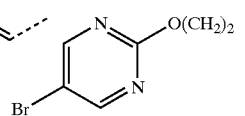 | 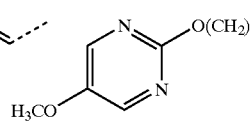 | $t_R$ = 5.63<br>$[M + H]^+$:584.08 | 1 |
| 42 | 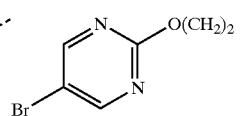 | 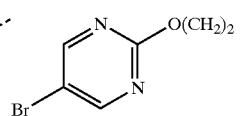 | $t_R$ = 5.27<br>$[M + H]^+$:534.28 | 1 |
TABLE 10
: Prep. according to Ex:
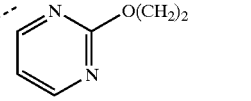
| Ex. No. | R¹ | R² | LC-MS | # |
|---|---|---|---|---|
| 43 | 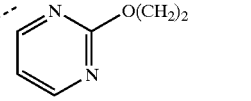 | 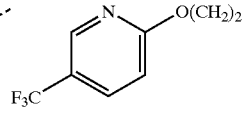 | $t_R$ = 5.45<br>$[M + H]^+$:590.01 | 1 |
| 44 | 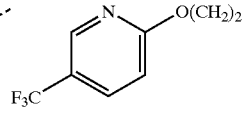 | 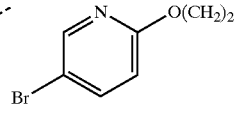 | $t_R$ = 4.95<br>$[M + H]^+$:510.19 | 1 |
| 45 | 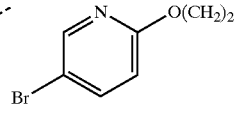 | 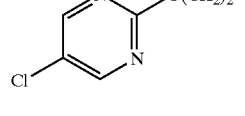 | $t_R$ = 5.88<br>$[M + H]^+$:577.14 | 5 |
| 46 | 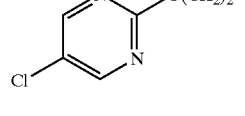 | 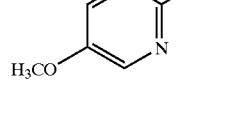 | $t_R$ = 5.89<br>$[M + H]^+$:588.38 | 5 |
| 47 | 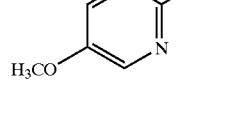 | 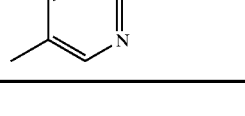 | $t_R$ = 5.36<br>$[M + H]^+$:545.4 | 1 |
| 48 | 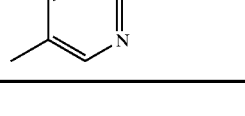 |  | $t_R$ = 5.15<br>$[M + H]^+$:541.46 | 1 |
| 49 |  |  | $t_R$ = 5.16<br>$[M + H]^+$:525.44 | 1 |

TABLE 11

: Prep. according to Ex:

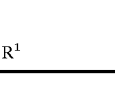

| Ex. No. | R¹ | R² | LC-MS | # |
|---|---|---|---|---|
| 50 | phenyl-CH=CH- | 5-fluoro-pyrimidin-2-yl-O(CH₂)₂- | $t_R$ = 5.18<br>[M − H]⁺:526.16 | 1 |
| 51 | phenyl-CH=CH- | 5-(methylthio)-pyrimidin-2-yl-O(CH₂)₂- | $t_R$ = 5.38<br>[M + H]⁺:555.98 | 1 |
| 52 | 3-methylphenyl-CH=CH- | 5-bromo-pyrimidin-2-yl-O(CH₂)₂- | $t_R$ = 5.65<br>[M + H]⁺:604.26 | 1 |
| 53 | 3-methylphenyl-CH=CH- | 5-methoxy-pyrimidin-2-yl-O(CH₂)₂- | $t_R$ = 5.29<br>[M + H]⁺:555.61 | 1 |

TABLE 12

: Prep. according to Ex:

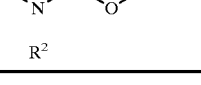

| Ex. No. | R¹ | R² | LC-MS | # |
|---|---|---|---|---|
| 54 | 4-chlorophenyl-CH=CH- | 5-bromo-pyrimidin-2-yl-O(CH₂)₂- | $t_R$ = 5.67<br>[M + H]⁺:624.20 | 1 |

TABLE 12-continued
: Prep. according to Ex:
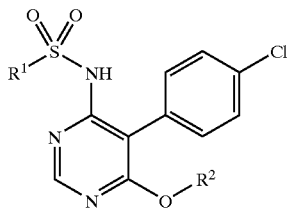
| Ex. No. | R¹ | R² | LC-MS | # |
|---|---|---|---|---|
| 55 | 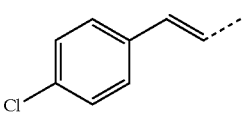 | 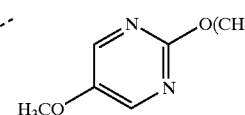 | $t_R$ = 5.34<br>[M + H]⁺:575.43 | 1 |
| 56 | 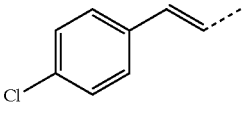 | 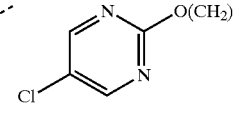 | $t_R$ = 5.59<br>[M + H]⁺:579.45 | 1 |
| 57 | 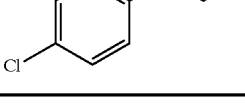 | 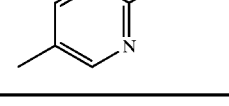 | $t_R$ = 5.42<br>[M + H]⁺:559.50 | 1 |
TABLE 13
: Prep. according to Ex:
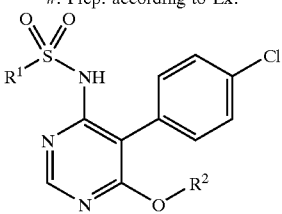
| Ex. No. | R¹ | R² | LC-MS | # |
|---|---|---|---|---|
| 58 | 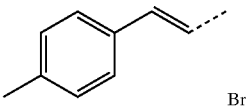 | 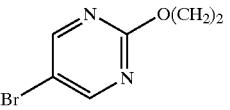 | $t_R$ = 5.61<br>[M + H]⁺:603.36 | 1 |
| 59 | 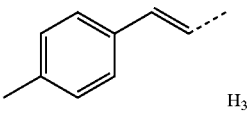 | 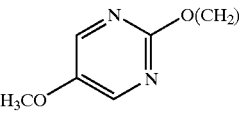 | $t_R$ = 5.26<br>[M + H]⁺:555.53 | 1 |
| 60 | 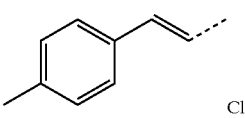 | 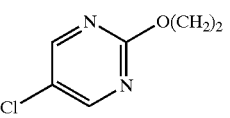 | $t_R$ = 5.55<br>[M + H]⁺:559.52 | 1 |
| 61 | 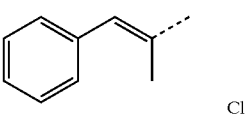 | 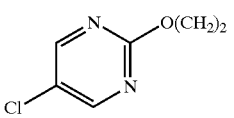 | $t_R$ = 5.46<br>[M + H]⁺:559.53 | 1 |

TABLE 13-continued
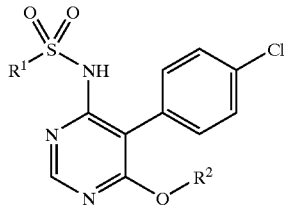
| Ex. No. | R¹ | R² | LC-MS | # |
|---|---|---|---|---|
| 62 | 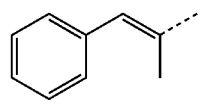 | 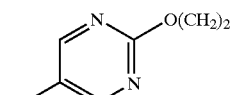 | $t_R$ = 5.51<br>[M + H]⁺:604.33 | 1 |
| 63 | 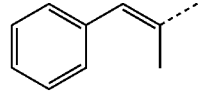 | 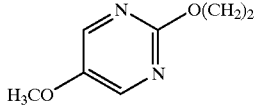 | $t_R$ = 5.16<br>[M + H]⁺:555.57 | 1 |
TABLE 14
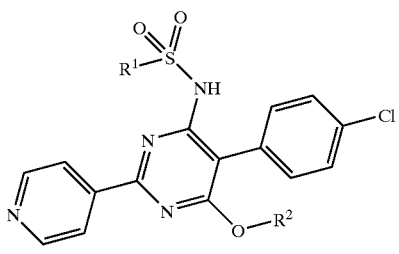
| Ex. No. | R¹ | R² | LC-MS | # |
|---|---|---|---|---|
| 64 | 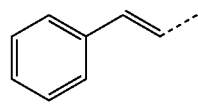 | 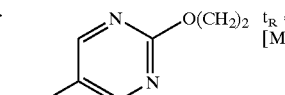 | $t_R$ = 4.98<br>[M + H]⁺:616.51 | 1 |
| 65 | 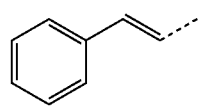 | 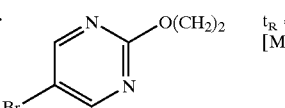 | $t_R$ = 5.35<br>[M + H]⁺:667.33 | 1 |
| 66 | 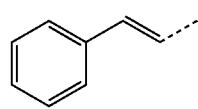 | 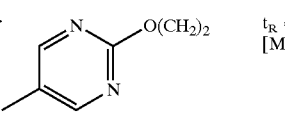 | $t_R$ = 5.00<br>[M + H]⁺:601.51 | 1 |

TABLE 15
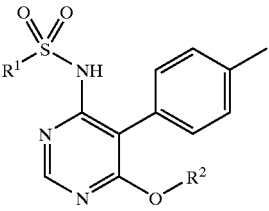
| Ex. No. | R¹ | R² | LC-MS | # |
|---|---|---|---|---|
| 67 | 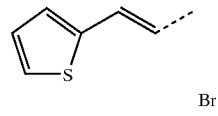 | 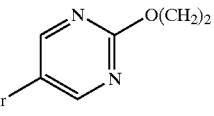 | $t_R$ = 5.34 [M + H]⁺:576.18 | 1 |
| 68 | 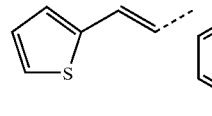 | 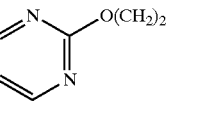 | $t_R$ = 4.79 [M + H]⁺:496.16 | 1 |
| 69 | 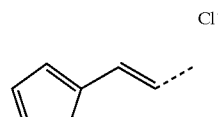 | 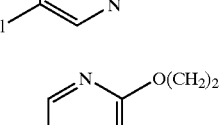 | $t_R$ = 5.26 [M + H]⁺:530.32 | 1 |
| 70 | 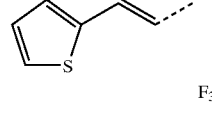 | 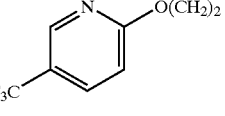 | $t_R$ = 5.79 [M + H]⁺:563.24 | 5 |
| 71 | 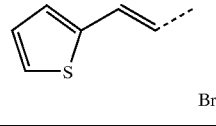 | 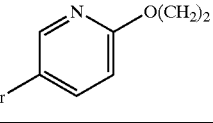 | $t_R$ = 5.78 [M + H]⁺:574.80 | 5 |
TABLE 16
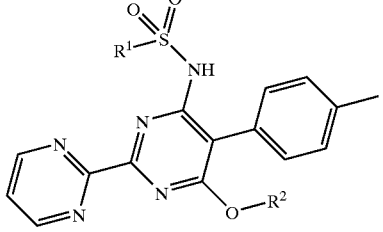
| Ex. No. | R¹ | R¹⁵ | LC-MS | # |
|---|---|---|---|---|
| 72 | 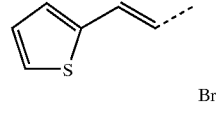 | 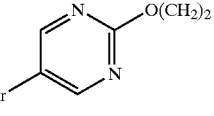 | $t_R$ = 5.28 [M + H]⁺:653.50 | 1 |
| 73 | 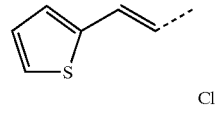 | 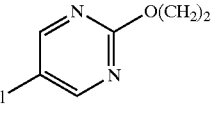 | $t_R$ = 5.25 [M + H]⁺:609.35 | 1 |

TABLE 16-continued

: Prep. according to Ex:

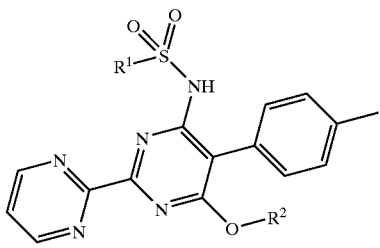

| Ex. No. | R¹ | R¹⁵ | LC-MS | # |
|---|---|---|---|---|
| 74 | 2-thienyl-CH=CH- | pyrimidine with H₃CO and O(CH₂)₂ | $t_R = 4.93$<br>$[M + H]^+$:604.02 | 1 |
| 75 | 2-thienyl-CH=CH- | 5-methylpyrimidin-2-yl-O(CH₂)₂ | $t_R = 4.81$<br>$[M + H]^+$:588.16 | 1 |

TABLE 17

: Prep. according to Ex:

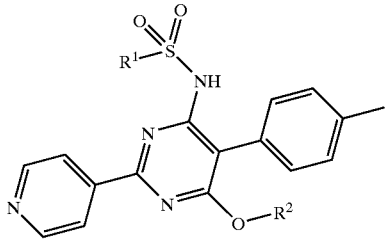

| Ex. No. | R¹ | R² | LC-MS | # |
|---|---|---|---|---|
| 76 | Ph-CH=CH- | Ph-O(CH₂)₃ | $t_R = 5.98$<br>$[M + H]^+$:579.41 | 3 |
| 77 | Ph-CH=CH- | 4-Br-Ph-O(CH₂)₂ | $t_R = 6.09$<br>$[M + H]^+$:645.28 | 3 |
| 78 | Ph-CH=CH- | Ph-O(CH₂)₂ | $t_R = 5.72$<br>$[M + H]^+$:565.22 | 3 |
| 79 | Ph-CH=CH- | pyrimidin-2-yl-O(CH₂)₂ | $t_R = 4.82$<br>$[M + H]^+$:567.20 | 1 |

TABLE 17-continued
: Prep. according to Ex:
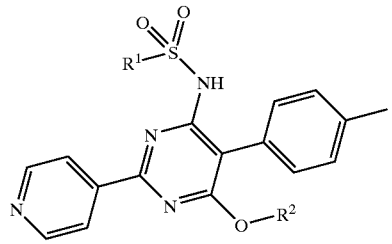
| Ex. No. | R¹ | R² | LC-MS | # |
|---|---|---|---|---|
| 80 | styryl | 5-Br-pyrimidin-2-yl-O(CH₂)₂ | $t_R$ = 5.45<br>[M + H]⁺:647.41 | 1 |
| 81 | styryl | 5-Br-pyridin-2-yl-O(CH₂)₂ | $t_R$ = 5.82<br>[M + H]⁺:646.07 | 5 |
| 82 | styryl | 5-CF₃-pyridin-2-yl-O(CH₂)₂ | $t_R$ = 5.83<br>[M + H]⁺:633.87 | 5 |
TABLE 18
: Prep. according to Ex:
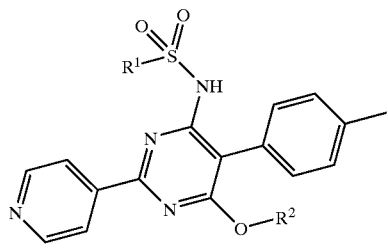
| Ex. No. | R¹ | R² | LC-MS | # |
|---|---|---|---|---|
| 83 | styryl | 5-OCH₃-pyrimidin-2-yl-O(CH₂)₂ | $t_R$ = 4.93<br>[M + H]⁺:597.26 | 1 |
| 84 | styryl | 5-Cl-pyrimidin-2-yl-O(CH₂)₂ | $t_R$ = 5.21<br>[M + H]⁺:602.60 | 1 |

TABLE 19
: Prep. according to Ex:
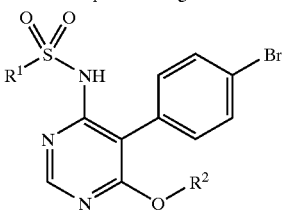
| Ex. No. | R¹ | R² | LC-MS | # |
|---|---|---|---|---|
| 85 | 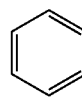 | 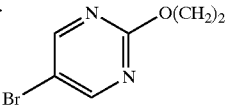 | $t_R$ = 5.78<br>$[M - H]^+$:632.25 | 1 |
| 86 | 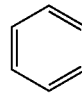 | 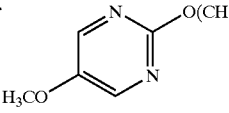 | $t_R$ = 5.33<br>$[M + H]^+$:585.83 | 1 |
| 87 | 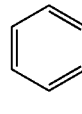 | 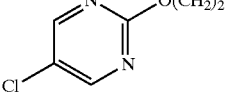 | $t_R$ = 5.65<br>$[M + H]^+$:589.70 | 1 |
| 88 | 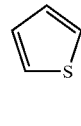 | 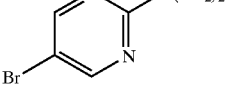 | $t_R$ = 5.45<br>$[M + H]^+$:641.33 | 1 |
| 89 | 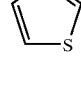 | 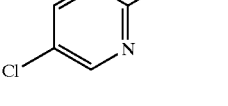 | $t_R$ = 5.39<br>$[M + H]^+$:596.31 | 1 |
| 90 | 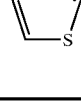 | 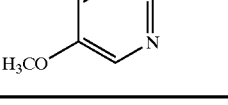 | $t_R$ =5.09<br>$[M + H]^+$:591.74 | 1 |
TABLE 20
: Prep. according to Ex:
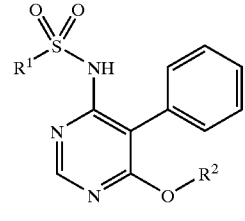
| Ex. No. | R¹ | R² | LC-MS | # |
|---|---|---|---|---|
| 91 | 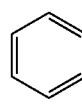 | 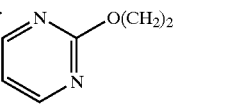 | $t_R$ = 4.78<br>$[M + H]^+$:476.23 | 1 |

TABLE 20-continued

: Prep. according to Ex:

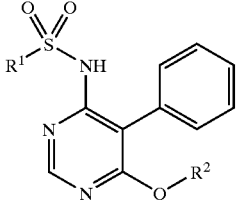

| Ex. No. | R¹ | R² | LC-MS | # |
|---|---|---|---|---|
| 92 | phenyl-CH=CH- | 5-Br-pyrimidin-2-yl-O(CH$_2$)$_2$ | $t_R$ = 5.30<br>[M + H]⁺:556.16 | 1 |
| 93 | phenyl-CH=CH- | 5-CF$_3$-pyridin-2-yl-O(CH$_2$)$_2$ | $t_R$ = 5.68<br>[M + H]⁺:543.34 | 5 |
| 94 | phenyl-CH=CH- | 5-Br-pyridin-2-yl-O(CH$_2$)$_2$ | $t_R$ = 5.68<br>[M + H]⁺:554.95 | 5 |
| 95 | phenyl-CH=CH- | 5-CF$_3$-pyrimidin-2-yl-O(CH$_2$)$_2$ | $t_R$ = 5.30<br>[M + H]⁺:544.13 | 1 |
| 96 | phenyl-CH=CH- | 5-OCH$_3$-pyrimidin-2-yl-O(CH$_2$)$_2$ | $t_R$ = 4.87<br>[M + H]⁺:506.14 | 1 |

TABLE 21

: Prep. according to Ex:

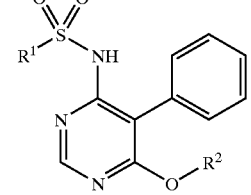

| Ex. No. | R¹ | R² | LC-MS | # |
|---|---|---|---|---|
| 97 | 4-Cl-phenyl-CH=CH- | 5-OCH$_3$-pyrimidin-2-yl-O(CH$_2$)$_2$ | $t_R$ = 5.14<br>[M − H]⁺:538.09 | 1 |
| 98 | 4-Cl-phenyl-CH=CH- | pyrimidin-2-yl-O(CH$_2$)$_2$ | $t_R$ = 4.96<br>[M − H]⁺:508.36 | 1 |

TABLE 21-continued

\#: Prep. according to Ex:

[Structure: R¹-S(=O)(=O)-NH-pyrimidine(5-phenyl)-O-R²]

| Ex. No. | R¹ | R² | LC-MS | # |
|---|---|---|---|---|
| 99 | 4-Cl-phenyl-CH=CH- | 5-Br-pyrimidin-2-yl-O(CH₂)₂ | $t_R$ = 5.46 [M + H]⁺:590.22 | 1 |

TABLE 22

\#: Prep. according to Ex:

[Structure: Ph-CH=CH-S(=O)(=O)-NH-pyrimidine(5-phenyl, 2-R¹, 4-OR²)]

| Ex. No. | R¹ | R² | LC-MS | # |
|---|---|---|---|---|
| 100 | H₃C-S- | pyrimidin-2-yl-O(CH₂)₂ | $t_R$ = 5.39 [M + H]⁺: 522.30 | 1 |
| 101 | H₃C-S- | 5-Br-pyrimidin-2-yl-O(CH₂)₂ | $t_R$ = 5.95 [M + H]⁺: 602.20 | 1 |
| 102 | F₃C- | 5-CF₃-pyridin-2-yl-O(CH₂)₂ | $t_R$ = 6.18 [M − H]⁺: 608.71 | 5 |
| 103 | F₃C- | pyrimidin-2-yl-O(CH₂)₂ | $t_R$ = 5.33 [M + H]⁺: 544.21 | 1 |

TABLE 22-continued

\#: Prep. according to Ex:

[Structure: Ph-CH=CH-S(=O)(=O)-NH-pyrimidine(5-phenyl, 2-R¹, 4-OR²)]

| Ex. No. | R¹ | R² | LC-MS | # |
|---|---|---|---|---|
| 104 | phenyl | 5-Br-pyrimidin-2-yl-O(CH₂)₂ | $t_R$ = 6.03 [M + H]⁺: 633.49 | 1 |
| 105 | phenyl | 5-Cl-pyrimidin-2-yl-O(CH₂)₂ | $t_R$ = 5.97 [M + H]⁺: 588.00 | 1 |
| 106 | phenyl | 5-OCH₃-pyrimidin-2-yl-O(CH₂)₂ | $t_R$ = 5.71 [M + H]⁺: 582.35 | 1 |

TABLE 23

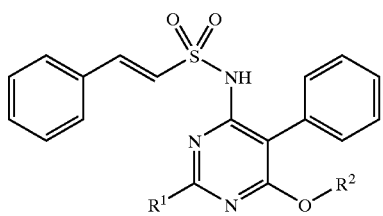

\#: Prep. according to Ex:

| Ex. No. | R¹ | R² | LC-MS | # |
|---|---|---|---|---|
| 107 | H₃C-S(O)₂- | 5-Br-pyrimidin-2-yl-O(CH₂)₂ | $t_R$ = 5.14, [M + H]⁺: 634.06 | 1 |
| 108 | pyridin-4-yl | 5-Cl-pyrimidin-2-yl-O(CH₂)₂ | $t_R$ = 5.02, [M + H]⁺: 589.66 | 1 |
| 109 | pyridin-4-yl | 5-Br-pyrimidin-2-yl-O(CH₂)₂ | $t_R$ = 5.08, [M + H]⁺: 633.65 | 1 |
| 110 | pyridin-4-yl | 5-H₃CO-pyrimidin-2-yl-O(CH₂)₂ | $t_R$ = 4.69, [M + H]⁺: 583.04 | 1 |
| 111 | pyrimidin-2-yl | 5-Br-pyrimidin-2-yl-O(CH₂)₂ | $t_R$ = 5.06, [M + H]⁺: 634.35 | 1 |
| 112 | pyrimidin-2-yl | 5-H₃CO-pyrimidin-2-yl-O(CH₂)₂ | $t_R$ = 4.73, [M + H]⁺: 584.08 | 1 |
| 113 | CH₃OCH₂CH₂O- | 5-Br-pyrimidin-2-yl-O(CH₂)₂ | $t_R$ = 5.42, [M + H]⁺: 629.77 | 1 |

TABLE 24

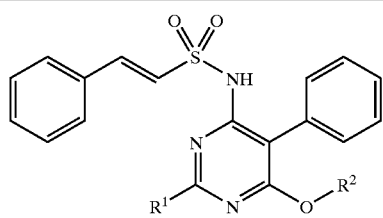

\#: Prep. according to Ex:

| Ex. No. | R¹ | R² | LC-MS | # |
|---|---|---|---|---|
| 114 | H₃CO- | pyrimidin-2-yl-O(CH₂)₂ | $t_R$ = 5.46, [M + H]⁺: 585.59 | 1 |

TABLE 26

Structure: styryl-SO2-NH-[pyrimidine with 5-(p-tolyl), 2-R¹, 6-OR²]

| Ex. No. | R¹ | R² | LC-MS | # |
|---|---|---|---|---|
| 125 | pyrazin-2-yl | 5-bromopyrimidin-2-yl-O(CH₂)₂ | $t_R$ = 5.44 [M + H]⁺: 648.30 | 1 |
| 126 | pyrazin-2-yl | 5-methoxypyrimidin-2-yl-O(CH₂)₂ | $t_R$ = 5.11 [M + H]⁺: 598.31 | 1 |
| 127 | morpholin-4-yl | 5-bromopyrimidin-2-yl-O(CH₂)₂ | $t_R$ = 5.85 [M + H]⁺: 655.22 | 1 |
| 128 | morpholin-4-yl | 5-methoxypyrimidin-2-yl-O(CH₂)₂ | $t_R$ = 5.42 [M + H]⁺: 605.26 | 1 |
| 129 | morpholin-4-yl | pyrimidin-2-yl-O(CH₂)₂ | $t_R$ = 5.33 [M + H]⁺: 575.41 | 1 |
| 130 | morpholin-4-yl | 5-(trifluoromethyl)pyridin-2-yl-O(CH₂)₂ | $t_R$ = 6.26 [M + H]⁺: 642.16 | 5 |
| 131 | morpholin-4-yl | 5-bromopyridin-2-yl-O(CH₂)₂ | $t_R$ = 6.28 [M + H]⁺: 654.03 | 5 |

TABLE 27

| Ex. No. | R¹ | R² | LC-MS | # |
|---|---|---|---|---|
| 132 | cyclopropyl | 5-bromopyrimidin-2-yl-O(CH₂)₂ | $t_R$ = 6.01 [M + H]⁺: 610.22 | 1 |

TABLE 27-continued

| Ex. No. | R¹ | R² | LC-MS | # |
|---|---|---|---|---|
| 133 | cyclopropyl | 5-methoxypyrimidin-2-yl-O(CH₂)₂ | $t_R$ = 5.59 [M + H]⁺: 560.25 | 1 |
| 134 | cyclopropyl | 5-chloropyrimidin-2-yl-O(CH₂)₂ | $t_R$ = 5.92 [M – H]⁺: 562.15 | 1 |
| 135 | cyclopropyl | pyrimidin-2-yl-O(CH₂)₂ | $t_R$ = 5.51 [M + H]⁺: 530.33 | 1 |
| 136 | cyclopropyl | 5-bromopyridin-2-yl-O(CH₂)₂ | $t_R$ = 6.48 [M + H]⁺: 608.32 | 5 |
| 137 | cyclopropyl | 5-(trifluoromethyl)pyridin-2-yl-O(CH₂)₂ | $t_R$ = 6.44 [M + H]⁺: 597.12 | 5 |

TABLE 28

| Ex. No. | R¹ | R² | LC-MS | # |
|---|---|---|---|---|
| 138 | CH₃ | 5-bromopyrimidin-2-yl-O(CH₂)₂ | $t_R$ = 5.66 [M + H]⁺: 583.99 | 1 |
| 139 | CH₃ | 5-methoxypyrimidin-2-yl-O(CH₂)₂ | $t_R$ = 5.30 [M + H]⁺: 534.18 | 1 |

TABLE 28-continued
: Prep. according to Ex:
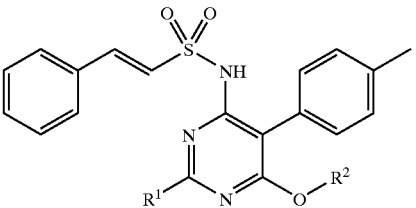
| Ex. No. | R¹ | R² | LC-MS | # |
|---|---|---|---|---|
| 140 | 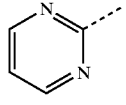 | 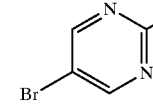 | $t_R$ = 5.23 [M + H]⁺: 648.19 | 1 |
| 141 | 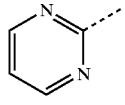 | 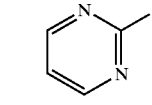 | $t_R$ = 4.85 [M + H]⁺: 568.32 | 1 |
| 142 | 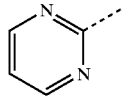 | 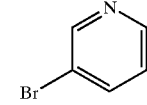 | $t_R$ = 5.63 [M + H]⁺: 646.77 | 5 |
| 143 | 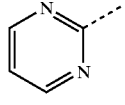 | 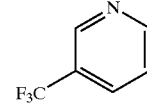 | $t_R$ = 5.68 [M + H]⁺: 635.30 | 5 |
| 144 | 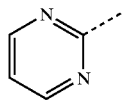 | 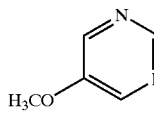 | $t_R$ = 5.02 [M + H]⁺: 598.01 | 1 |
TABLE 29
: Prep. according to Ex:
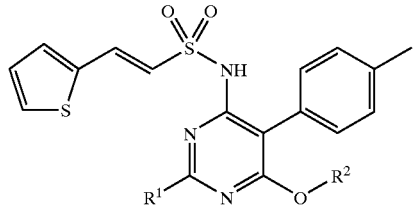
| Ex. No. | R¹ | R² | LC-MS | # |
|---|---|---|---|---|
| 145 | 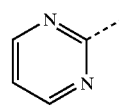 | 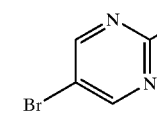 | $t_R$ = 5.28 [M + H]⁺: 653.50 | 1 |
| 146 | 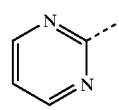 | 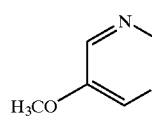 | $t_R$ = 4.93 [M + H]⁺: 604.02 | 1 |
| 147 | 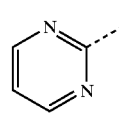 | 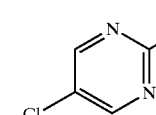 | $t_R$ = 5.25 [M + H]⁺: 608.35 | 1 |
| 148 | 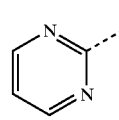 | 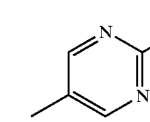 | $t_R$ = 4.81 [M + H]⁺: 588.16 | 1 |

TABLE 30
| Ex. No. | R¹ | R² | LC-MS | # |
|---|---|---|---|---|
| 149 | phenyl-CH=CH- | 5-bromo-pyrimidin-2-yl-O(CH₂)₂ | $t_R$ = 5.14 [M + H]⁺: 680.44 | 1 |
| 150 | phenyl-CH=CH- | 5-methoxy-pyrimidin-2-yl-O(CH₂)₂ | $t_R$ = 4.71 [M + H]⁺: 630.28 | 1 |
| 151 | phenyl-CH=CH- | 5-methyl-pyrimidin-2-yl-O(CH₂)₂ | $t_R$ = 4.73 [M + H]⁺: 614.10 | 1 |
| 152 | phenyl-CH=CH- | pyrimidin-2-yl-O(CH₂)₂ | $t_R$ = 4.65 [M + H]⁺: 600.44 | 1 |
| 153 | phenyl-CH=CH- | 4-bromo-phenyl-O(CH₂)₂ | $t_R$ = 5.68 [M + H]⁺: 678.22 | 3 |
| 154 | phenyl-CH=CH- | phenyl-O(CH₂)₂ | $t_R$ = 5.41 [M + H]⁺: 598.40 | 3 |
| 155 | 4-Cl-phenyl-CH=CH- | pyrimidin-2-yl-O(CH₂)₂ | $t_R$ = 4.96 [M + H]⁺: 634.34 | 1 |
TABLE 31
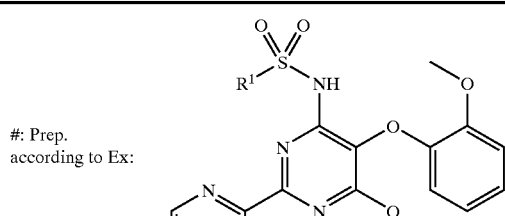

Example 242
Using methods described in the above Examples and in schemes 1 to 3 and the cited references, the compounds disclosed in Table 46 can be prepared:
TABLE 46
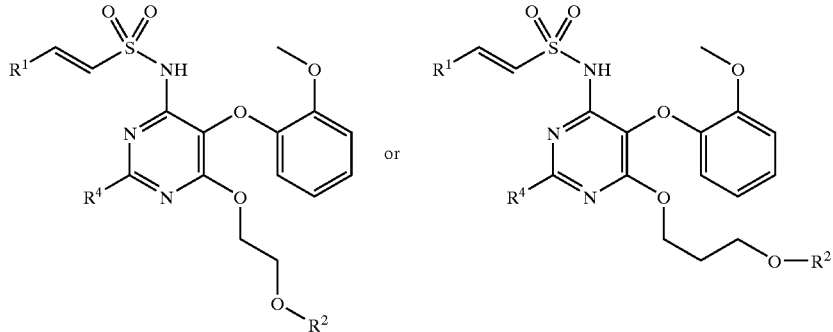

TABLE 46-continued
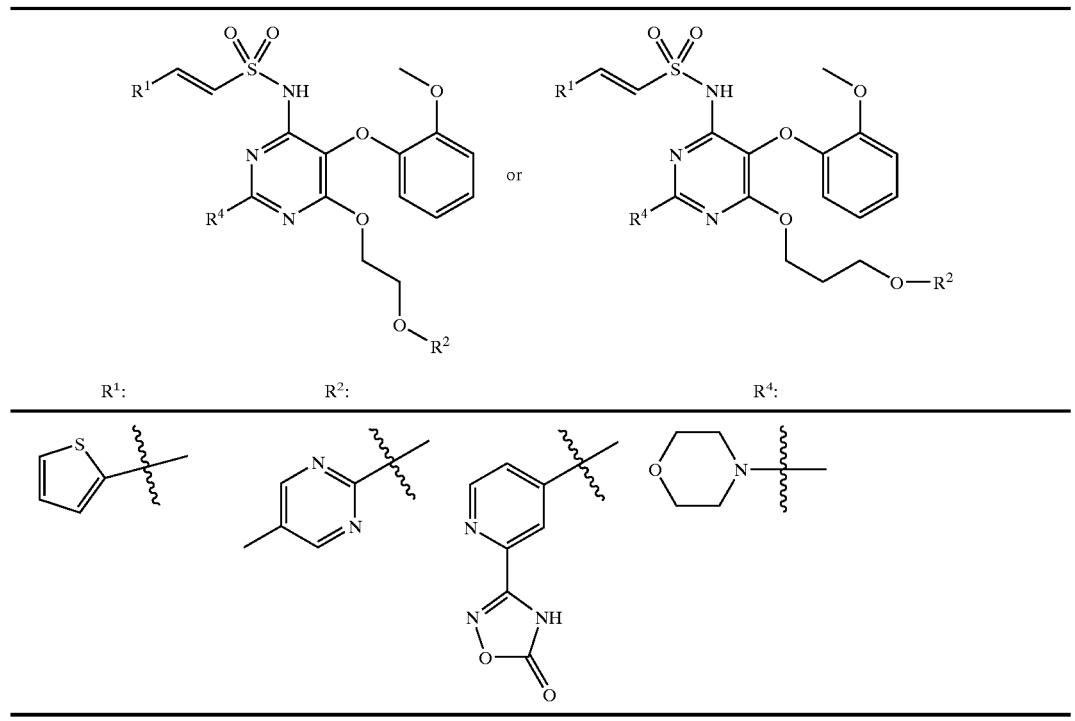
— indicates the connection of the substituents to the respective atom of the core unit
Example 243
Using methods described in the above Examples and in schemes 1 to 3 and in the cited references, the compounds disclosed in Table 47 can be prepared:

TABLE 47

List of Abbreviations:
CyHex cyclohexane
DCM dichloromethane
DMF dimethylformamide
DMSO dimethylsulfoxide
EA ethyl acetate
Hex hexane
HV high vacuum conditions
MCPBA m-chloroperbenzoic acid
min minutes
rt room temperature
THF tetrahydrofuran
$t_R$ retention time

What is claimed is:

1. A compound of the formula I

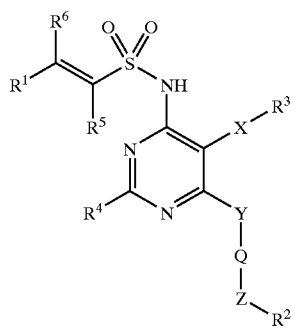

General Formula I wherein $R^1$ and $R^2$ are individually aryl or heteroaryl;

$R^3$ is phenyl, mono-, di- or tri-substituted phenyl substituted with lower alkyl, lower alkenyl, lower alkynyl, phenyl, lower alkyloxy, amino, lower alkylamino, amino-lower alkyl, trifluoromethyl, trifluoromethoxy, halogen, lower alkylthio, hydroxy, hydroxy-lower alkyl, cyano, carboxyl, lower alkanoyl, formyl, benzofuranyl, aryl or heteroaryl;

$R^4$ is hydrogen, halogen, trifluoromethyl, lower alkyl, lower alkyl-amino, lower alkyloxy, lower alkyl-sulfono, lower alkyl-sulfinyl, lower alkylthio, lower alkylthio-lower alkyl, hydroxy-lower alkyl, lower alkyl-oxy-lower alkyl, hydroxy-lower alkyl-oxy-lower alkyl, hydroxy-lower alkyl-amino, lower alkyl-amino-lower alkyl, amino, di-lower alkyl-amino, [N-(hydroxy-lower alkyl)-N-(lower alkyl)]-amino, aryl, aryl-amino, aryl-lower alkyl-amino, aryl-thio, aryl-lower alkyl-thio, aryloxy, aryl-lower alkyl-oxy, aryl-lower alkyl, aryl-sulfinyl, heteroaryl, heteroaryl-oxy, heteroaryl-lower alkyl-oxy, heteroaryl-amino, heteroaryl-lower alkyl-amino, heteroaryl-thio, heteoroaryl-lower alkyl-thio, heteroaryl-lower alkyl, heteroaryl-sulfinyl, heterocyclyl, heterocyclyl-lower alkyl-oxy, heterocyclyl-oxy, heterocyclyl-amino, heterocyclyl-lower alkyl-amino, heterocyclyl-thio, heterocyclyl-lower alkyl-thio, heterocyclyl-lower alkyl, heterocyclyl-sulfinyl, cycloalkyl, cycloalkyl-oxy, cycloalkyl-lower alkyl-oxy, cycloalkyl-amino, cycloalkyl-lower alkyl-amino, cycloalkyl-thio, cycloalkyl-lower alkyl-thio, cycloalkyl-lower alkyl, cycloalkyl-sulfinyl;

$R^5$ and $R^6$ are individually hydrogen or lower alkyl;

X is oxygen, sulfur, NH, $CH_2$ or a bond;

Y is oxygen, sulfur or —NH—;

Z is oxygen, sulfur, —NH— or a bond;

Q is —$(CH_2)_n$— or —$(CH_2)_m$—C≡C—$(CH_2)_p$—, and when p is the whole number 0, Z is a bond or —$CH_2$-cyclopropylen-$CH_2$—;

n is the whole numbers 2, 3, 4, 5 or 6;

m is the whole numbers 1, 2 or 3;

p is the whole numbers 0, 1, 2 or 3; or pharmaceutically acceptable salts thereof.

2. The compounds of claim 1, wherein $R^1$, $R^2$, $R^4$, $R^5$, $R^6$, Q, Y and Z are as defined in claim 1, X, is oxygen and $R^3$ is phenyl or mono-substituted phenyl substituted with halogen, lower alkyl, lower alkylene lower alkoxy, amino, lower alkyl-amino, lower alkyl-thio, hydroxy, hydroxymethyl or lower alkanoyl.

3. The compounds of claim 1, wherein $R^1$, $R^2$, $R^4$, $R^5$, $R^6$ and Q are as defined in claim 1, X, Y and Z represent individually oxygen and $R^3$ is di-substituted phenyl substituted with halogen or lower alkoxy.

4. The compounds of claim 1, wherein $R^1$, $R^2$, $R^4$, $R^5$, $R^6$ and Q are as defined in claim 1, X, V and Z are individually oxygen and $R^3$ is mono-substituted phenyl substituted with halogen, lower alkyl or lower alkoxy.

5. The compounds of claim 1, wherein $R^1$, $R^2$, $R^4$, $R^5$ and $R^6$ are as defined in claim 1, X, V and Z are individually oxygen, Q is —$(CH_2)_n$— with n=2 and $R^3$ is phenyl, mono- or di-substituted phenyl substituted with halogen, lower alkyl or lower alkoxy.

6. The compounds of claim 1, wherein $R^1$, $R^4$, $R^5$ and $R^6$ are as defined in claim 1, X, Y and Z are individually oxygen, Q is —$(CH_2)_n$— with n=2 $R^2$ is heteroaryl and $R^3$ is phenyl, mono- or di-substituted phenyl substituted with halogen, lower alkyl or lower alkoxy.

7. The compounds of claim 1 having the formula:

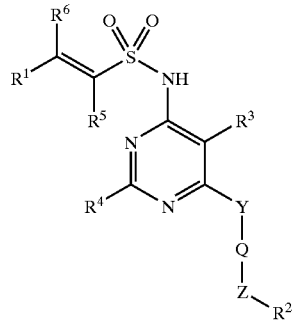

Formula II wherein $R^1$, $R^2$, $R^3$, $R^4$, $R^5$, $R^6$, Y, Q and Z are as defined in claim 1, or pharmaceutically acceptable salts thereof compound.

8. The compound of claim 1 having the formula:

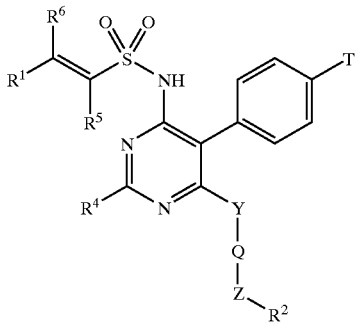

Formula III wherein $R^1$, $R^2$, $R^4$, $R^5$, $R^6$, Y, Q and Z are as defined in claim 1 and T is a chlorine-, a bromine- or a hydrogen-atom or a methyl group or a methoxy group or pharmaceutically acceptable salts thereof.

9. The compounds of claim 7 having the formula:

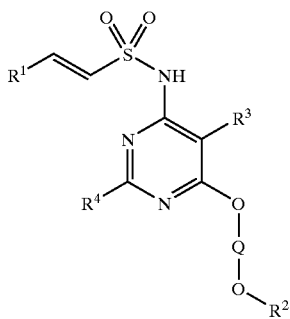

Formula IV wherein $R^1$, $R^2$, $R^3$, $R^4$ and Q are as defined in claim 1 or pharmaceutically acceptable salts thereof.

10. The compound of claim 8 having the formula:

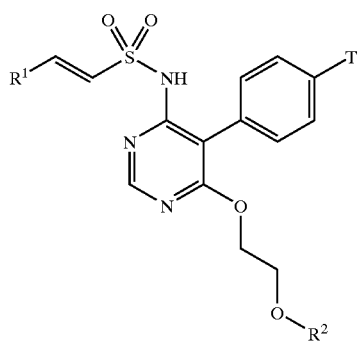

Formula V wherein $R^1$ and $R^2$ are as defined in claim 1 and T is chlorine-, a bromine- or a hydrogen-atom or a methyl group or a methoxy group or pharmaceutically acceptable salts thereof.

11. The compound of claim 10, wherein $R^2$ is heteroaryl or pharmaceutically acceptable salts thereof.

12. The compound of claim 1 wherein said compound is one of the following:
2-Phenyl-ethenesulfonic acid [6-[2-(5-bromo-pyrimidin-2-yloxy)-ethoxy]-5-p-tolyl-pyrimidin-4-yl]-amide;
2-Phenyl-ethenesulfonic acid {5-(4-bromo-phenyl)-6-[2-(5-bromo-pyrimi-din-2-yloxy)-ethoxy]-pyrimidin-4-yl}-amide;
2-Phenyl-ethenesulfonic acid {6-[2-(5-bromo-pyrimidin-2-yloxy)-ethoxy]-5-phenyl-pyrimidin-4-yl}-amide;
2-Phenyl-ethenesulfonic acid {6-[2-(5-chloro-pyrimidin-2-yloxy)-ethoxy]-5-p-tolyl-pyrimidin-4-yl}-amide;
2-Phenyl-ethenesulfonic acid {6-[2-(4-bromo-phenoxy)-ethoxy]-5-p-tolyl-pyrimidin-4-yl}-amide;
2-Thiophen-3-yl-ethenesulfonic acid {6-[2-(5-bromo-pyrimidin-2-yloxy)-ethoxy]-5-p-tolyl-pyrimidin-4-yl}-amide;
2-Thiophen-2-yl-ethenesulfonic acid {6-[2-(5-bromo-pyrimidin-2-yloxy)-ethoxy]-5-p-tolyl-pyrimidin-4-yl}-amide;
2-Thiophen-2-yl-ethenesulfonic acid {6-[2-(5-bromo-pyrimidin-2-yloxy)-ethoxy]-5-p-tolyl-[2,2']bipyrimidinyl-4-yl)-amide;
2-Phenyl-ethenesulfonic acid {6-[2-(5-bromo-pyrimidin-2-yloxy)-ethoxy]-5-p-totyl-[2,2']bipyrimidinyl-4-yl)-amide;
2-Phenyl-ethenesulfonic acid (6-[2-(5-bromo-pyrimidin-2-yioxy)-ethoxy]-5-(2-methoxy-phenoxy)-pyrimidin-4-yl]-amide;
2-Phenyl-ethenesulfonic acid [6-[2-(5-bromo-pyrimidin-2-yloxy)-ethoxy]-5-(3-methoxy-phenoxy)-pyrimidin-4-yl]-amide;
2-Phenyl-ethenesulfonic acid [6-[2-(5-bromo-pyrimidin-2-yloxy)-ethoxy]-5-(2-methoxy-phenoxy)-2-pyrazin-2-yl-pyrimidin-4-yl]-amide;
2-Phenyl-ethenesulfonic acid [6-[2-(5-bromo-pyrimidin-2-yloxy)-ethoxy]-5-(2-methoxy-phenoxy)-2-morpholin-4-yl-pyrimidin-4-yl]-amide;
2-Phenyl-ethenesulfonic acid {5-(2-methoxy-phenoxy)-2-morpholin-4-yl-6-[2-(5-trifluoromethyl-pyrimidin-2-yloxy)-ethoxy]-pyrimidin-4-yl}-amide;
2-Phenyl-ethenesulfonic acid {5-(2-methoxy-phenoxy)-6-[2-(pyrimidin-2-yloxy)-ethoxy]-[2,2']bipyrimidinyl-4-yl}-amide;
2-Thiophen-2-yl-ethenesulfonic acid [6-[2-(5-bromo-pyrimidin-2-yloxy)-ethoxy]-5-(2-methoxy-phenoxy)-[2,2']bipyrimidinyl-4-yl]-amide;
2-Thiophen-2-yl-ethenesulfonic acid [6-[2-(5-bromo-pyrimidin-2-yloxy)-ethoxy]-5-(2-methoxy-phenoxy)-2-pyridin-4-yl-pyrimidin-4-yl]-amide;
2-Phenyl-ethenesulfonic acid [6-[2-(5-bromo-pyrimidin-2-yloxy)-ethoxy]-5-(2-chloro-5-methoxy-phenoxy)-pyrimidin-4-yl]-amide;
2-Phenyl-ethenesulfonic acid [6-[2-(5-bromo-pyrimidin-2-yloxy)-ethoxy]-5-(4-chloro-phenyl)-pyrimidin-4-yl]-amide;
2-Phenyl-ethenensulfonic acid }6-[2-(5-bromo-pyrimidin-2-yloxy)-ethoxy]-2-pyridin-4-yl-5-p-tolyl-pyrimidin-4-yl}-amide;
or pharmaceutically acceptable salts thereof.

13. The compound of claim 11 wherein $R^1$ is phenyl.

14. The compound of claim 13 wherein said compound is 2-phenyl-ethenesulfonic acid [6-[2-(5-bromo-pyrimidin-2-yloxy)-ethoxy]-5-(4-chloro-phenyl)-pyrimidin-4-yl]-amide or pharmaceutically acceptable salts thereof.

15. The compound of claim 13 wherein said compound is 2-phenyl-ethenesulfonic acid {6-[2-(5-bromo-primidin-2-yloxy)-ethoxy]-2-pyridin-4-yl-5-p-tolyl-pyrimidin-4-yl}-amide or pharmaceutically acceptable salts thereof.

16. The compound of claim 13 wherein said compound is 2-phenyl-ethenesulfonic acid [6-[2-(5-bromo-pyrimidin-2-yloxy)-ethoxy]-5-p-tolyl-pyrimidin-4-yl]-amide or pharmaceutically acceptable salts thereof.

17. The compound of claim 13 wherein said compound is 2-phenyl-ethenesulfonic acid {5-[4-bromo-phenyl)-6-[2-(5- bromo-pyrimi-din-2-yloxy)-ethoxy]-pyrimidin-4-yl}-amide or pharmaceutically acceptable salts thereof.

18. The compound of claim 13 wherein said compound is 2-phenyl-ethenesulfonic acid {6-[2-(5-chloro-pyrimidin-2-yloxy)-ethoxy]-5-p-tolyl-pyrimidin-4-yl}-amide or pharmaceutically acceptable salts thereof.

19. The compound of claim 11 wherein $R^1$ is heteroaryl.

20. The compound of claim 19 wherein said compound is 2-thiophen-3-yl-ethenesulfonic acid {6-(2-(5-bromo-pyrimidin-2-yloxy)-ethoxy]-5-p-tolyl-pyrimidin-4-yl}-amide or pharmaceutically acceptable salts thereof.

21. The compound of claim 19 wherein said compound is 2-thiophen-2-yl-ethenesulfonic acid {6-[2-(5-bromo-pyrimidin-2-yloxy)-ethoxy]-5-p-tolyl-pyrimidin-4-yl}-amide or pharmaceutically acceptable salts thereof.

22. The compound of claim 10 wherein $R^2$ is aryl.

23. The compound of claim 22 wherein said compound is 2-phenyl-ethenesulfonic acid {6-[2-(4-bromo-phenoxy)-ethoxy]-5-p-tolyl-pyrimidin-4-yl}-amide or pharmaceutically acceptable salts thereof.

24. The compound of claim 8 wherein $R^1$ is phenyl and $R^4$ is heteroaryl.

25. The compound of claim 24 where said compound is 2-phenyl-ethenesulfonic acid {6-[2-(5-bromo-pyrimidin-2-yloxy)-ethoxy]-5-p-tolyl-[2,2']bipyrimidinyl-4-yl}-amide or pharmaceutically acceptable salts thereof.

26. The compound of claim 8 wherein is $R^1$ heteroaryl.

27. The compound of claim 24 wherein said compound is 2-thiophen-2-yl-ethenesulfonic acid {6-[2-(5-bromo-pyrimidin-2-yloxy)-ethoxy]-5p-tolyl-[2,2']bipyrimidinyl-4-yl}-amide or pharmaceutically acceptable salts thereof.

28. The compound of claim 6 wherein $R^1$ is aryl.

29. The compound of claim 28 wherein said compound is 2-phenyl-ethenesulfonic acid [6-[2-(5bromo-pyrimidin-2-yloxy)-ethoxy]-5-(2methoxy-phenoxy)-pyrimidin-4-yl]-amide or pharmaceutically acceptable salts thereof.

30. The compound of claim 28 wherein said compound is 2-phenyl-ethenesulfonic acid [6-[2-(5-bromo-pyrimidin-2-yloxy)-ethoxy]-5-(3-methoxy-phenoxy)-pyrimidin-4-yl]-amide or pharmaceutically acceptable salts thereof.

31. The compound of claim 28 wherein said compound is 2-phenyl-ethenesulfonic acid [6-[2-(5-bromo-pyrimidin-2-yloxy)-ethoxy]-5-(2-methoxy-phenoxy)-2-pyrazin-2-yl-pyrimidin-4-yl]-amide or pharmaceutically acceptable salts thereof.

32. The compound of claim 28 wherein said compound is 2-phenyl-ethenesulfonic acid [6-[2-(5-bromo-pyrimidin-2-yloxy)-ethoxy]-5-(2-methoxy-phenoxy)-2-morpholin-4-yl-pyrimidin-4-yl]-amide or pharmaceutically acceptable salts thereof.

33. The compound of claim 28 wherein said compound is 2-phenyl-ethenesulfonic acid {5-(2-methoxy-phenoxy)-2-morpholin-4-yl-6-[2-(5-trifluoromethyl-pyrimidin-2-yloxy)-ethoxy]-pyrimidin-4-yl}-amide or pharmaceutically acceptable salts thereof.

34. The compound of claim 28 wherein said compound is 2-phenyl-ethenesulfonic acid {5-(2-methoxy-phenoxy)-6-[2-(pyrimidin-2yloxy)-ethoxy]-[2 2']bipyrimidinyl-4-yl}-amide or pharmaceutically acceptable salts thereof.

35. The compound of claim 28 wherein said compound is 2-phenyl-ethenesulfonic acid [6-[2-(5-bromo-pyrimidin-2-yloxy)-ethoxy]-5-(2-chloro-5-methoxy-phenoxy)-pyrimidin-4-yl]-amide or pharmaceutically acceptable salts thereof.

36. The compound of claim 6 wherein $R^1$ is heteroaryl.

37. The compound of claim 36 wherein said compound is 2-thiophen-2-yl-ethenesulfonic acid [6-[2-(5-bromo-pyrimidin-2-yloxy)-ethoxy]-5-(2-methoxy-phenoxy)-[2,2'] bipyrimidinyl-4-yl]-amide or pharmaceutically acceptable salts thereof.

38. The compound of claim 36 wherein said compound is 2-thiophen-2-yl-ethenesulfonic acid [6-[2-(5-bromo-pyrimidin-2-yloxy)-ethoxy]-5-(2-methoxy-phenoxy)-2-pyridin-4-yl-pyrimidin-4-yl]-amide or pharmaceutically acceptable salts thereof.

* * * * *

UNITED STATES PATENT AND TRADEMARK OFFICE
CERTIFICATE OF CORRECTION

PATENT NO. : 6,951,856 B2
APPLICATION NO. : 10/332247
DATED : October 4, 2005
INVENTOR(S) : Boss et al.

It is certified that error appears in the above-identified patent and that said Letters Patent is hereby corrected as shown below:

In Column 84, line 28 (claim 4, line 2), please change "V" to read --Y--;

In Column 84, line 32 (claim 5, line 2), please change "V" to read --Y--

Signed and Sealed this

Twenty-sixth Day of December, 2006

JON W. DUDAS
*Director of the United States Patent and Trademark Office*